(12) United States Patent
Mika et al.

(10) Patent No.: US 7,840,262 B2
(45) Date of Patent: Nov. 23, 2010

(54) APPARATUS AND METHOD FOR DELIVERING ELECTRICAL SIGNALS TO MODIFY GENE EXPRESSION IN CARDIAC TISSUE

(75) Inventors: Yuval Mika, Zichron-Yaakov (IL); Hani N. Sabbah, Detroit, MI (US); Walid Haddad, Closter, NJ (US); Benny Rousso, Rishon-Lezion (IL)

(73) Assignee: Impulse Dynamics NV, Curacao (AN)

( * ) Notice: Subject to any disclaimer, the term of this patent is extended or adjusted under 35 U.S.C. 154(b) by 431 days.

(21) Appl. No.: 10/549,216

(22) PCT Filed: Mar. 10, 2004

(86) PCT No.: PCT/US2004/007589

§ 371 (c)(1),
(2), (4) Date: Oct. 12, 2006

(87) PCT Pub. No.: WO2004/080533

PCT Pub. Date: Sep. 23, 2004

(65) Prior Publication Data

US 2007/0027487 A1     Feb. 1, 2007

Related U.S. Application Data

(60) Provisional application No. 60/453,349, filed on Mar. 10, 2003, provisional application No. 60/503,075, filed on Sep. 15, 2003.

(51) Int. Cl.
*A61N 1/00* (2006.01)
(52) U.S. Cl. ............................... 607/2; 607/3
(58) Field of Classification Search .................... 607/2, 607/3
See application file for complete search history.

(56) References Cited

U.S. PATENT DOCUMENTS

| | | |
|---|---|---|
| 1,918,386 A | 7/1933 | Esau |
| 3,541,390 A | 11/1970 | Jahnke |
| 3,572,345 A | 3/1971 | Auphan |
| 3,587,567 A | 6/1971 | Schiff |
| 3,651,805 A | 3/1972 | Breiling |
| 3,651,806 A | 3/1972 | Hirshberg |
| 3,796,221 A | 3/1974 | Hagfors |
| 3,911,930 A | 10/1975 | Hagfors et al. |
| 3,933,147 A | 1/1976 | Du Vall et al. |
| 3,942,536 A | 3/1976 | Mirowski et al. |
| 3,944,740 A | 3/1976 | Murase et al. |
| 3,952,750 A | 4/1976 | Mirowski et al. |

(Continued)

FOREIGN PATENT DOCUMENTS

EP     0148687     7/1985

(Continued)

OTHER PUBLICATIONS

Gardner, David G., "Natriuretic peptides: markers or modulators of cardiac hypertrophy?", Nov. 2003, TRENDS in Endocrinology and Metabolism, vol. 14 No. 9, pp. 411-416.*

(Continued)

*Primary Examiner*—Carl H Layno
*Assistant Examiner*—Yun Haeng Lee

(57) ABSTRACT

Method and apparatus (120) for modifying gene expression in cardiac muscle cells (110), by the application of electric fields.

52 Claims, 4 Drawing Sheets

GAPDH

ANP

α-MHC

BNP bFGF

U.S. PATENT DOCUMENTS

| | | |
|---|---|---|
| 4,030,509 A | 6/1977 | Heilman et al. |
| 4,055,190 A | 10/1977 | Tany |
| 4,106,494 A | 8/1978 | McEachern |
| 4,164,216 A | 8/1979 | Person |
| 4,168,711 A | 9/1979 | Cannon, III et al. |
| 4,184,493 A | 1/1980 | Langer et al. |
| 4,202,340 A | 5/1980 | Langer et al. |
| 4,223,678 A | 9/1980 | Langer et al. |
| 4,237,895 A | 12/1980 | Johnson |
| 4,273,114 A | 6/1981 | Barkalow et al. |
| 4,293,734 A | 10/1981 | Pepper, Jr. |
| 4,312,354 A | 1/1982 | Walters |
| 4,316,472 A | 2/1982 | Mirowski et al. |
| 4,337,776 A | 7/1982 | Daly et al. |
| 4,384,585 A | 5/1983 | Zipes |
| 4,387,717 A | 6/1983 | Brownlee et al. |
| 4,403,614 A | 9/1983 | Engle et al. |
| 4,406,288 A | 9/1983 | Horwinski et al. |
| 4,407,288 A | 10/1983 | Langer et al. |
| 4,411,268 A | 10/1983 | Cox |
| 4,428,366 A | 1/1984 | Findl et al. |
| 4,440,172 A | 4/1984 | Langer |
| 4,506,680 A | 3/1985 | Stokes |
| 4,537,195 A | 8/1985 | McDonnell |
| 4,537,203 A | 8/1985 | Machida |
| 4,543,956 A | 10/1985 | Herscovici |
| 4,550,221 A | 10/1985 | Mabusth |
| 4,554,922 A | 11/1985 | Prystowsky et al. |
| 4,554,992 A | 11/1985 | Kassai |
| 4,559,946 A | 12/1985 | Mower |
| 4,566,456 A | 1/1986 | Koning et al. |
| 4,572,191 A | 2/1986 | Mirowski et al. |
| 4,628,934 A | 12/1986 | Pohndorf et al. |
| 4,639,720 A | 1/1987 | Rympalski et al. |
| 4,651,716 A | 3/1987 | Forester et al. |
| 4,674,508 A | 6/1987 | DeCote |
| 4,679,572 A | 7/1987 | Baker, Jr. |
| 4,686,332 A | 8/1987 | Greanias et al. |
| 4,690,155 A | 9/1987 | Hess |
| 4,726,279 A | 2/1988 | Kepler et al. |
| 4,726,379 A | 2/1988 | Altman et al. |
| 4,765,341 A | 8/1988 | Mower et al. |
| 4,830,006 A | 5/1989 | Haluska et al. |
| 4,834,100 A | 5/1989 | Charms |
| 4,850,959 A | 7/1989 | Findl |
| 4,870,974 A | 10/1989 | Wang |
| 4,878,553 A | 11/1989 | Yamanami et al. |
| 4,914,624 A | 4/1990 | Dunthorn et al. |
| 4,928,688 A | 5/1990 | Mower |
| 4,967,749 A | 11/1990 | Cohen |
| 4,979,507 A | 12/1990 | Heinz et al. |
| 4,988,837 A | 1/1991 | Murakami et al. |
| 4,998,531 A | 3/1991 | Bocchi et al. |
| 5,002,052 A | 3/1991 | Haluska et al. |
| 5,003,976 A | 4/1991 | Alt |
| 5,020,544 A | 6/1991 | Dahl et al. |
| 5,022,396 A | 6/1991 | Watanabe |
| 5,026,397 A | 6/1991 | Aoki et al. |
| 5,031,617 A | 7/1991 | Klettner |
| 5,044,375 A | 9/1991 | Bach, Jr. et al. |
| 5,083,564 A | 1/1992 | Scherlag |
| 5,085,218 A | 2/1992 | Heil et al. |
| 5,087,243 A | 2/1992 | Avitall |
| 5,097,832 A | 3/1992 | Buchanan |
| 5,097,833 A | 3/1992 | Campos |
| 5,097,843 A | 3/1992 | Soukup et al. |
| 5,101,814 A | 4/1992 | Palti |
| 5,111,815 A | 5/1992 | Mower |
| 5,129,394 A | 7/1992 | Mehra |
| 5,133,354 A | 7/1992 | Kallok |
| 5,137,021 A | 8/1992 | Wayne et al. |
| 5,144,554 A | 9/1992 | Zhang et al. |
| 5,156,147 A | 10/1992 | Warren et al. |
| 5,156,149 A | 10/1992 | Hudrlik |
| 5,161,527 A | 11/1992 | Nappholz et al. |
| 5,163,428 A | 11/1992 | Pless |
| 5,172,690 A | 12/1992 | Nappholz et al. |
| 5,174,286 A | 12/1992 | Chirife |
| 5,188,104 A | 2/1993 | Wernicke et al. |
| 5,188,106 A | 2/1993 | Nappholz et al. |
| 5,190,036 A | 3/1993 | Linder |
| 5,190,041 A | 3/1993 | Palti |
| 5,199,428 A | 4/1993 | Obel et al. |
| 5,205,284 A | 4/1993 | Freeman |
| 5,213,098 A | 5/1993 | Bennett et al. |
| 5,231,381 A | 7/1993 | Duwaer |
| 5,231,988 A | 8/1993 | Wernicke et al. |
| 5,236,413 A | 8/1993 | Feiring |
| 5,282,785 A | 2/1994 | Shapland et al. |
| 5,284,491 A | 2/1994 | Sutton et al. |
| 5,286,254 A | 2/1994 | Shapland et al. |
| 5,292,344 A | 3/1994 | Douglas |
| 5,305,745 A | 4/1994 | Zacouto |
| 5,320,543 A | 6/1994 | Roline et al. |
| 5,320,642 A | 6/1994 | Scherlag et al. |
| 5,320,643 A | 6/1994 | Roline et al. |
| 5,324,327 A | 6/1994 | Cohen |
| 5,327,887 A | 7/1994 | Nowakowski |
| 5,346,506 A | 9/1994 | Mower et al. |
| 5,350,403 A | 9/1994 | Stroetmann et al. |
| 5,353,800 A | 10/1994 | Pohndorf et al. |
| 5,365,461 A | 11/1994 | Stein et al. |
| 5,366,486 A | 11/1994 | Zipes et al. |
| 5,368,040 A | 11/1994 | Carney |
| 5,370,665 A | 12/1994 | Hudrlik |
| 5,381,160 A | 1/1995 | Landmeier |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben-Haim |
| 5,397,344 A | 3/1995 | Garfield et al. |
| 5,398,683 A | 3/1995 | Edwards et al. |
| 5,402,151 A | 3/1995 | Duwaer |
| 5,411,531 A | 5/1995 | Hill et al. |
| 5,415,629 A | 5/1995 | Henley |
| 5,417,717 A | 5/1995 | Salo et al. |
| 5,419,763 A | 5/1995 | Hildebrand |
| 5,423,872 A | 6/1995 | Cigaina |
| 5,425,363 A | 6/1995 | Wang |
| 5,431,688 A | 7/1995 | Freeman |
| 5,431,693 A | 7/1995 | Schroeppel |
| 5,433,730 A | 7/1995 | Alt |
| 5,443,485 A | 8/1995 | Housworth et al. |
| 5,445,609 A | 8/1995 | Lattin et al. |
| 5,447,520 A | 9/1995 | Spano et al. |
| 5,447,526 A | 9/1995 | Karsdon |
| 5,458,568 A | 10/1995 | Racchini et al. |
| 5,464,020 A | 11/1995 | Lerner |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,497 A | 12/1995 | Mower et al. |
| 5,482,052 A | 1/1996 | Lerner |
| 5,499,971 A | 3/1996 | Shapland et al. |
| 5,501,662 A | 3/1996 | Hofmann |
| 5,510,813 A | 4/1996 | Makinwa et al. |
| 5,514,162 A | 5/1996 | Bornzin et al. |
| 5,520,642 A | 5/1996 | Bigagli et al. |
| 5,528,002 A | 6/1996 | Katabami |
| 5,531,764 A | 7/1996 | Adams et al. |
| 5,534,015 A | 7/1996 | Kroll et al. |
| 5,540,722 A | 7/1996 | Clare et al. |
| 5,540,730 A | 7/1996 | Terry, Jr. et al. |

| Patent | Date | Name |
|---|---|---|
| 5,540,734 A | 7/1996 | Zabara |
| 5,543,588 A | 8/1996 | Bisset et al. |
| 5,543,589 A | 8/1996 | Buchana et al. |
| 5,556,421 A | 9/1996 | Prutchi et al. |
| 5,556,760 A | 9/1996 | Nakamura et al. |
| 5,561,165 A | 10/1996 | Lautt et al. |
| 5,565,632 A | 10/1996 | Ogawa |
| 5,568,809 A | 10/1996 | Ben-haim |
| 5,571,143 A | 11/1996 | Hoegnelid et al. |
| 5,571,997 A | 11/1996 | Gray et al. |
| 5,578,061 A | 11/1996 | Stroetmann et al. |
| 5,584,803 A | 12/1996 | Stevens et al. |
| 5,584,804 A | 12/1996 | Klatz et al. |
| 5,584,868 A | 12/1996 | Salo et al. |
| 5,587,200 A | 12/1996 | Lorenz et al. |
| 5,589,856 A | 12/1996 | Stein et al. |
| 5,601,609 A | 2/1997 | Duncan |
| 5,601,611 A | 2/1997 | Fayram et al. |
| 5,622,687 A | 4/1997 | Krishnan et al. |
| 5,626,622 A | 5/1997 | Cooper |
| 5,632,267 A | 5/1997 | Högnelid et al. |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,670,755 A | 9/1997 | Kwon |
| 5,674,251 A | 10/1997 | Combs et al. |
| 5,674,259 A | 10/1997 | Gray |
| 5,683,431 A | 11/1997 | Wang |
| 5,687,734 A | 11/1997 | Dempsey et al. |
| 5,690,691 A | 11/1997 | Chen et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben-Haim |
| 5,738,105 A | 4/1998 | Kroll |
| 5,741,791 A | 4/1998 | Olsen |
| 5,749,906 A | 5/1998 | Kieval et al. |
| 5,755,740 A | 5/1998 | Nappholz |
| 5,777,607 A | 7/1998 | Koolen |
| 5,779,661 A | 7/1998 | Stephen et al. |
| 5,782,876 A | 7/1998 | Flammang |
| 5,782,881 A | 7/1998 | Lu et al. |
| 5,790,106 A | 8/1998 | Hirano et al. |
| 5,792,189 A | 8/1998 | Gray et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,824,016 A | 10/1998 | Ekwall |
| 5,825,352 A | 10/1998 | Bisset et al. |
| 5,841,078 A | 11/1998 | Miller et al. |
| 5,844,506 A | 12/1998 | Binstead |
| 5,854,881 A | 12/1998 | Yoshida et al. |
| 5,861,014 A | 1/1999 | Familoni |
| 5,861,583 A | 1/1999 | Schediwy et al. |
| 5,865,787 A | 2/1999 | Shapland et al. |
| 5,871,506 A | 2/1999 | Mower |
| 5,906,607 A | 5/1999 | Taylor et al. |
| 5,913,876 A | 6/1999 | Taylor et al. |
| 5,919,216 A | 7/1999 | Houben et al. |
| 5,927,284 A | 7/1999 | Borst et al. |
| 5,954,761 A | 9/1999 | Machek et al. |
| 5,956,020 A | 9/1999 | D'Amico et al. |
| 5,962,246 A | 10/1999 | Ladner et al. |
| 5,991,649 A | 11/1999 | Garfield et al. |
| 5,995,872 A | 11/1999 | Bourgeois |
| 6,006,134 A | 12/1999 | Hill et al. |
| 6,023,640 A | 2/2000 | Ross |
| 6,026,326 A | 2/2000 | Bardy |
| 6,032,074 A | 2/2000 | Collins |
| 6,032,672 A | 3/2000 | Taylor |
| 6,037,882 A | 3/2000 | Levy |
| 6,041,252 A | 3/2000 | Walker et al. |
| 6,057,374 A | 5/2000 | Huntington et al. |
| 6,066,163 A | 5/2000 | John |
| 6,067,470 A | 5/2000 | Mower |
| 6,071,305 A | 6/2000 | Brown et al. |
| 6,083,249 A | 7/2000 | Familoni |
| 6,086,582 A | 7/2000 | Altman et al. |
| 6,093,167 A | 7/2000 | Houben et al. |
| 6,128,007 A | 10/2000 | Seybold et al. |
| 6,133,906 A | 10/2000 | Geaghan |
| 6,135,978 A | 10/2000 | Houben et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,233,484 B1 | 5/2001 | Ben-Haim et al. |
| 6,239,389 B1 | 5/2001 | Allen et al. |
| 6,243,607 B1 | 6/2001 | Mintchev et al. |
| 6,261,280 B1 | 7/2001 | Houben et al. |
| 6,278,443 B1 | 8/2001 | Amro et al. |
| 6,285,906 B1 | 9/2001 | Ben-Haim et al. |
| 6,292,693 B1 | 9/2001 | Darvish et al. |
| 6,292,704 B1 | 9/2001 | Malonek et al. |
| 6,295,470 B1 | 9/2001 | Mower |
| 6,296,693 B1 | 10/2001 | McCarthy |
| 6,298,254 B2 | 10/2001 | Tamada |
| 6,298,268 B1 | 10/2001 | Ben-Haim et al. |
| 6,317,631 B1 | 11/2001 | Ben-Haim et al. |
| 6,330,476 B1 | 12/2001 | Ben-Haim |
| 6,337,995 B1 | 1/2002 | Mower |
| 6,341,235 B1 | 1/2002 | Mower |
| 6,343,232 B1 | 1/2002 | Mower |
| 6,363,279 B1 | 3/2002 | Ben-Haim et al. |
| 6,381,495 B1 | 4/2002 | Jenkins |
| 6,392,636 B1 | 5/2002 | Ferrari et al. |
| 6,411,847 B1 | 6/2002 | Mower |
| 6,415,178 B1 | 7/2002 | Ben-Haim et al. |
| 6,417,846 B1 | 7/2002 | Lee |
| 6,424,864 B1 | 7/2002 | Matsuura |
| 6,433,069 B1 | 8/2002 | Oeltjen et al. |
| 6,449,511 B1 | 9/2002 | Mintchev et al. |
| 6,452,514 B1 | 9/2002 | Philipp |
| 6,463,323 B1 | 10/2002 | Conrad-Vlasak et al. |
| 6,463,324 B1 | 10/2002 | Ben-Haim et al. |
| 6,469,719 B1 | 10/2002 | Kino et al. |
| 6,473,069 B1 | 10/2002 | Gerpheide |
| 6,504,530 B1 | 1/2003 | Wilson et al. |
| 6,505,745 B1 | 1/2003 | Anderson |
| 6,507,093 B2 | 1/2003 | Kaneda et al. |
| 6,555,235 B1 | 4/2003 | Aufderheide et al. |
| RE38,119 E | 5/2003 | Mower |
| 6,558,345 B1 | 5/2003 | Houben et al. |
| 6,570,557 B1 | 5/2003 | Westerman et al. |
| 6,571,127 B1 | 5/2003 | Ben-Haim et al. |
| 6,572,542 B1 | 6/2003 | Houben et al. |
| 6,583,676 B2 | 6/2003 | Krah et al. |
| 6,587,093 B1 | 7/2003 | Shaw et al. |
| 6,587,721 B1 | 7/2003 | Prutchi et al. |
| 6,600,953 B2 | 7/2003 | Flesler et al. |
| 6,611,258 B1 | 8/2003 | Tanaka et al. |
| 6,612,983 B1 | 9/2003 | Marchal |
| 6,630,123 B1 | 10/2003 | Woltering et al. |
| 6,633,280 B1 | 10/2003 | Matsumoto et al. |
| 6,652,444 B1 | 11/2003 | Ross |
| 6,658,297 B2 | 12/2003 | Loeb |
| 6,667,740 B2 | 12/2003 | Ely et al. |
| 6,684,104 B2 | 1/2004 | Gordon et al. |
| 6,690,156 B1 | 2/2004 | Weiner et al. |
| 6,762,752 B2 | 7/2004 | Perski et al. |

| | | |
|---|---|---|
| 6,810,286 B2 | 10/2004 | Donovan et al. |
| 6,919,205 B2 | 7/2005 | Brighton |
| 6,949,081 B1 | 9/2005 | Chance |
| 7,006,871 B1 | 2/2006 | Darvish et al. |
| 7,076,306 B2 | 7/2006 | Marchal et al. |
| 7,092,753 B2 | 8/2006 | Darvish et al. |
| 7,440,806 B1 | 10/2008 | Whitehurst et al. |
| 2002/0026141 A1 | 2/2002 | Houben et al. |
| 2002/0081732 A1 | 6/2002 | Bowlin et al. |
| 2002/0161414 A1 | 10/2002 | Flesler et al. |
| 2002/0183682 A1 | 12/2002 | Darvish et al. |
| 2002/0183686 A1 | 12/2002 | Darvish et al. |
| 2003/0018367 A1 | 1/2003 | DiLorenzo |
| 2003/0055464 A1 | 3/2003 | Darvish et al. |
| 2003/0100889 A1 | 5/2003 | Duverger et al. |
| 2003/0181958 A1 | 9/2003 | Dobak, III |
| 2003/0188899 A1 | 10/2003 | Chao et al. |
| 2003/0208242 A1 | 11/2003 | Harel et al. |
| 2004/0059393 A1 | 3/2004 | Policker et al. |
| 2004/0105040 A1 | 6/2004 | Oh et al. |
| 2004/0106954 A1 | 6/2004 | Whitehurst et al. |
| 2004/0155871 A1 | 8/2004 | Perski et al. |
| 2004/0158289 A1* | 8/2004 | Girouard et al. ............... 607/3 |
| 2004/0230273 A1 | 11/2004 | Cates et al. |
| 2004/0249421 A1 | 12/2004 | Harel et al. |
| 2005/0033396 A1 | 2/2005 | Ospyka |
| 2005/0192542 A1 | 9/2005 | Dev et al. |
| 2006/0097991 A1 | 5/2006 | Hotelling et al. |
| 2006/0184207 A1 | 8/2006 | Darvish et al. |
| 2007/0171211 A1 | 7/2007 | Perski et al. |
| 2008/0058879 A1 | 3/2008 | Ben-Haim et al. |
| 2008/0065159 A1 | 3/2008 | Ben-Haim et al. |
| 2008/0065163 A1 | 3/2008 | Ben-Haim et al. |
| 2008/0065164 A1 | 3/2008 | Ben-Haim et al. |
| 2009/0131993 A1 | 5/2009 | Rousso et al. |
| 2009/0292324 A1 | 11/2009 | Rousso et al. |

FOREIGN PATENT DOCUMENTS

| | | |
|---|---|---|
| EP | 0156593 | 10/1985 |
| EP | 0250931 | 1/1988 |
| EP | 0314078 | 5/1989 |
| EP | 0727241 | 8/1996 |
| EP | 1263498 | 12/2002 |
| GB | 1394171 | 5/1975 |
| JP | 04117967 | 4/1992 |
| JP | 4365493 | 12/1992 |
| JP | 07-503865 | 4/1995 |
| JP | 7126600 | 5/1995 |
| JP | 8243176 | 9/1996 |
| RU | 2014844 | 6/1994 |
| RU | 2055606 | 3/1996 |
| RU | 2075980 | 3/1997 |
| RU | 2077273 | 4/1997 |
| RU | 2078547 | 5/1997 |
| WO | WO 91/19534 | 12/1991 |
| WO | WO 92/00716 | 1/1992 |
| WO | WO 93/02743 | 2/1993 |
| WO | WO 93/18820 | 9/1993 |
| WO | WO 94/17855 | 8/1994 |
| WO | WO 95/08316 | 3/1995 |
| WO | WO 96/10358 | 4/1996 |
| WO | WO 97/15227 | 5/1997 |
| WO | WO 97/25098 | 7/1997 |
| WO | WO 97/25101 | 7/1997 |
| WO | WO 97/26042 | 7/1997 |
| WO | WO 97/27900 | 8/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/15317 | 4/1998 |
| WO | WO 98/56378 | 12/1998 |
| WO | WO 98/57701 | 12/1998 |
| WO | WO 99/03533 | 1/1999 |
| WO | WO 99/24110 | 5/1999 |
| WO | WO 99/29307 | 6/1999 |
| WO | WO 99/55360 | 11/1999 |
| WO | WO 99/59548 | 11/1999 |
| WO | WO 00/04947 | 2/2000 |
| WO | WO 00/12525 | 3/2000 |
| WO | WO 00/16741 | 3/2000 |
| WO | WO 00/27475 | 5/2000 |
| WO | WO 00/42914 | 7/2000 |
| WO | WO 00/53257 | 9/2000 |
| WO | WO 00/74773 | 12/2000 |
| WO | WO 01/24871 | 4/2001 |
| WO | WO 01/49367 | 7/2001 |
| WO | WO 01/52931 | 7/2001 |
| WO | WO 01/66183 | 9/2001 |
| WO | WO 01/91854 | 12/2001 |
| WO | WO 01/93950 | 12/2001 |
| WO | WO 01/93951 | 12/2001 |
| WO | WO 02/10791 | 2/2002 |
| WO | WO 02/053093 | 7/2002 |
| WO | WO 02/082968 | 10/2002 |
| WO | WO 03/045493 | 6/2003 |
| WO | WO 2004/021858 | 3/2004 |
| WO | WO 2004/070396 | 8/2004 |
| WO | WO 2005/023081 | 3/2005 |
| WO | WO 2005/087310 | 9/2005 |
| WO | WO 2005/114369 | 12/2005 |
| WO | WO 2006/073671 | 7/2006 |
| WO | WO 2006/087717 | 8/2006 |
| WO | WO 2006/097935 | 9/2006 |

OTHER PUBLICATIONS

Antoni et al. "Polarization Effects of Sinusoidal 50-Cycle Alternating Current on Membrane Potential of Mammalian Cardiac Fibres", Pflügers Archiv European Journal of Physiology, 314(4): 274-291, 1970.

Bakker et al. "Beneficial Effects of Biventricular Pacing of Congestive Heart Failure", Pace, 17(Part II): 318, 1994.

Bakker et al. "Biventricular Pacing Improves Functional Capacity in Patients With End-Stage Congestive Heart Failure", Pace, 17(11/Part II/120): 825, 1995.

Bargheer et al. "Prolongation of Monophastic Action Potantial Duration and the Refractory Period in the Human Heart by Tedisamil, A New Potassium-Blocking Agent", The European Society of Cardiology, 15(10): 1409-1414, 1994.

Burfeind et al. "The Effects of Mechanical Cardiac Stabilization on Left Ventricular Performance", European Journal of Cardio-Thoracic Surgery,14: 285-289, 1998.

Cazeau et al. "Multisite Pacing for End-Stage Heart Failure: Early Experience", PACE, 19(Part II): 1748-1757, 1996.

Cheng et al. "Calcium Sparks: Elementary Events Underlying Excitation-Contraction Coupling in Heart Muscle", Science, 262: 740-744, 1993.

Cooper "Postextrasystolic Potentiation: Do We Really Know What It Means and How to Use It?", Circulation, 88(6): 2962-2971, 1993.

Coulton et al. "Magnetic Fields and Intracellular Calcium: Effects on Lymphocytes Exposed to Conditions for 'Cyclotron Resonance'", Physics in Medicine and Biology, 38: 347-360, 1993.

Devedeux et al. "Uterine Electromyography: A Critical Review", American Journal of Obstetrics and Gynecology, 169(6): 1636-53, 1993.

Dillion "Optical Recordings in the Rabbit Heart Show That Defibrillation Strenght Shocks Prolong the Duration of Depolarization and the Refractory Period", Circulation Research, 69: 842-856, 1991.

Erol-Yilmaz et al. "Reversed Remodelling of Dilated Left Sided Cardiomyopathy After Upgrading From VVIR to VVIR Biventricular Pacing", Europace, 4: 445-449, 2002.

Fain et al. "Improved Internal Defibrillation Efficacy With A Biphasic Waveform", American Heart Journal, 117(2): 358-364, 1989.

Fleg et al. "Impact of Age on the Cardiovasvular Response to Dynamic Upright Exercise in Healthy Men and Women", Journal of Applied Physiology, 78: 890-900, 1995.

Foster et al. "Acute Hemodynamic Effects of Atrio—Biventricular Padng in Humans", The Society of Thoracic Surgeons, 59: 294-300, 1995.

Franz "Bridging the Gap Between Basic Clinical Electrophysiology: What Can Be Learned From Monophasic Action Potential Recordings?", Journal of Cardiovascular Electrophysiology, 5(8): 699-710, 1994.

Franz "Method and Theory of Monophasic Action Potential Recording", Progresses in Cardiovascular Diseases, 33(6): 347-368, 1991.

Fromer et al. "Ultrarapid Subthreshold Stimulation for Termination of Atriventricular Node Reentrant Tachycardia", Journal of the American College of Cardiology, 20(4): 879-883, 1992.

Fu et al. "System Identification of Electrically Coupled Smooth Muscle Cells: The Passive Electrically Coupled Smooth Muscle Cells: The Passive Electrical Properties", IEEE Transactions on Biomedical Engineering, 38(11): 1130-1140, 1991.

Gill et al. "Refractory Period Extension During Ventricular Pacing at Fibrillatory Pacing Rates", PACE, 20(Part I): 647-653, 1997.

Gomis et al. "Oscillatory Patterns of Electrical Activity in Mouse Pancreatic Islets of Langerhans Recorded In Vivo", Pflügers Archiv—European Journal of Physiology, 432(3): 510-515, 1996.

Hoffman et al. "Effects of Postextrasystolic Potentiation on Normal and Failing Hearts", Bulletin of the New York Academy of Medicine, 41(5): 498-534, 1965.

Horner et al. "Electrode for Recording Direction of Activation, Conduction Velocity, and Monophasic Action Potential of Myocardium", American Journal of Physiology, 272: H1917-H1927, 1997.

King et al. "The Inotropic Action of Paired Pulse Stimulation in the Normal and Failing Heart: An Experimental Study", Cardiovascular Research, 2: 122-129, 1968.

Kinsley et al. "Effect of Field Stimulation on Cellular Repolarization in Rabbit Myocardium Implications for Reentry Induction", Circulation Research, 70: 707-715, 1991.

Knisley et al. "Prolongation and Shortening of Action Potentials by Electrical Shocks in Frog Ventricular Muscle", American Journal of Physiology, 266: H2348-H2358, 1994.

Koller et al. "Relation Between Repolarization and Refractoriness During Programmed Electrical Stimulation in the Human Right Ventricle", Circulation, 91: 2378-2384, 1995.

Langberg et al. "Identification of Ventricular Tachycardia With Use of the Morphology of the Endocardial Electrogram", Circulation, 77: 1363-1369, 1988.

Lindström et al. "Intracellular Calcium Oscillations in A T-Cell Line After Exposure to Extremely-Low-Frequency Magnetic Fields With Variable Frequencies and Flux Densities", Bioelectromagnetics, 16: 41-47, 1995.

Mercando et al. "Automated Detection of Tachycardias by Antitachycardia Devices", Cardiac Electrophysiology: From Cell to Bedside, Chap.100: 943-948, 2004.

Paul et al. "Automatic Recognition of Ventricular Arrhythmias Using Temporal Electrogram Analysis", PACE, 14: 1265-1273, 1991.

Pumir et al. "Control of Rotating Waves in Cardiac Muscle: Analysis of the Effect of Electric Field", Proceedings of the Royal Society B: Biological Sciences, 257(1349): 129-134, 1994.

Xue et al. "Neural-Network-Based Adaptive Matched Filtering for QRS Detection", IEEE Transactions on Biomedical Engineering, 39(4): 317-329, 1992, Abstract.

Saihara "Summation of Excitation With A Single Conditioning Stimulus in the Canine Heart", PACE, 13: 52-58, 1990.

Sakuma et al. "A Model Analysis of Aftereffects of High-Intensity DC Stimulation on Action Potential of Ventricular Muscle", IEEE Transactions on Biomedical Engineering, 45(2): 258-267, 1998.

Skale et al. "Inhibition of Premature Ventricular Extrastimuli by Subthreshold Conditioning Stimuli", Journal of the American College of Cardiology, 6(1): 133-140, 1985.

Sweeney et al. "Refractory Interval After Transcardiac Shocks During Ventricular Fibrillation", Circulation, 94: 2947-2952, 1996.

Sweeney et al. "Ventricular Refractory Period Extension Caused by Defibrillation Shocks", Circulation, 82: 965-972, 1990.

Sweeny et al. "Countershock Strength-Duration Relationship for Myocardial Refractory Period Extension", Academy of Emergency Medicine, 2: 57-62, 1995.

Swerdlow et al. "Cardiovascular Collapse Caused by Electrocardiographically Silent 60-Hz Intracardiac Leakage Current: Implications for Electrical Safety", Circulation, 99: 2559-2564, 1999.

Talit et al. "The Effect of External Cardiac Pacing on Stroke Volume", PACE, 13: 598-602, 1990.

Taniguchi et al. "Inhomogeneity of Cellular Activation Time and VMax in Normal Myocardial Tissue Under Electrical Field Stimulation", American Journal of Physiology, 267: H694-H705, 1994.

Thakor et al. "Effect of Varying Pacing Waveform Shapes on Propagation and Hemodynamics in the Rabbit Heart", American Journal of Cardiology, 79(6A): 36-43, 1997.

Wessale et al. "Stroke Volume and the Three Phase Cardiac Output Rate Relationship With Ventricular Pacing", PACE, 13: 673-680, 1990.

Wirtzfeld et al. "Physiological Pacing: Present Status and Future Developments", PACE, 10(Pt.I): 41-57, 1987.

Yokoyama "The Phase of Supernormal Excitation in Relation to the Strength of Subthreshold Stimuli", Japanese Heart Journal, 17(3): 315-325, 1975.

Office Action Dated Nov. 2, 2007 From the Patent Office of the People's Republic of China Re.: Application No. 2004800009336.9.

Official Action Dated Dec. 5, 2008 From the US Patent and Trademark Office Re.: U.S. Appl. No. 11/550,560.

Official Action Dated Dec. 8, 2008 From the US Patent and Trademark Office Re.: U.S. Appl. No. 10/804,560.

Official Action Dated Dec. 24, 2008 From the US Patent and Trademark Office Re.: U.S. Appl. No. 10/237,263.

Supplementary European Search Report and the European Search Opinion Dated Nov. 28, 2008 From the European Patent Office Re.: Application No. 006759102.4.

Translation of the Examination Report Dated Apr. 3, 2008 From the Government of India, Patent Office Re.: Application No. 1821/CHENP/2005.

80 Request for Ex Parte Reexamination of US Patent No. 6,330,476—IDS filed May 31, 2006.

Amended Request for Ex Parte Reexamination of US Patent No. 6,317,631 Dated Aug. 20, 2007, U.S. Appl. No. 90/008,689.

Communication Pursuant to Article 94(3) EPC Dated Mar. 2, 2009 From the European Patent Office Re.: Application No. 05853465.2.

Communication Pursuant to Article 94(3) EPC Dated Jan. 28, 2009 From the European Patent Office Re.: Application No. 03794043.4.

Communication Pursuant to Article 94(3) EPC From the European Patent Office Re.: Application No. 04106247.2.

Communication to Pursuant to Article 94(3) EPC Dated Mar. 4, 2009 From the European Search Report Re.: Application No. 06759102.4.

Official Action Dated Mar. 6, 2009 From the US Patent and Trademark Office Re.: U.S. Appl. No. 11/931,889.

Official Action Dated Mar. 6, 2009 From the US Patent and Trademark Office Re.: U.S. Appl. No. 11/932,064.

Official Action Dated Jan. 21, 2009 From the US Patent and Trademark Office Re.: U.S. Appl. No. 10/570,576.

Official Action Dated Feb. 24, 2009 From the US Patent and Trademark Office Re.: U.S. Appl. No. 11/318,845.

Request for Ex Parte Reexamination of Patent No. 6,363,279—Notice of Intent to Issue Reexamination Certificate Dated Mar. 18, 2009, U.S. Appl. No. 90/008,688.

Request for Ex Parte Reexamination of Patent No. 6,363,279—Official Action Dated Jun. 20, 2008, U.S. Appl. No. 90/008,688.

Request for Ex Parte Reexamination of Patent No. 6,363,279—Order Granting Request Dated Nov. 5, 2007, U.S. Appl. No. 90/008,688.

Request for Ex Parte Reexamination of Patent No. 6,363,279 Dated Jun. 8, 2007, U.S. Appl. No. 90/008,688.

Request for Ex Parte Reexamination of Patent No. 6,363,279—IDS Submitted Dec. 31, 2007, U.S. Appl. No. 90/008,688.

Request for Ex Parte Reexamination of Patent No. 6,363,279, Response to Official Action Dated Jun. 20, 2008 Submitted Aug. 20, 2008, U.S. Appl. No. 90/008,688.

Request for Ex Parte Reexamination of US Patent No. 6,236,887—IDS Submitted Oct. 17, 2007, U.S. Appl. No. 90/008,707.
Request for Ex Parte Reexamination of US Patent No. 6,236,887—IDS Submitted Sep. 29, 2008, U.S. Appl. No. 90/008,707.
Request for Ex Parte Reexamination of US Patent No. 6,236,887—Notice of Intent to Issue Ex Parte Examination Certificate Dated Mar. 19, 2009, U.S. Appl. No. 90/008,707.
Request for Ex Parte Reexamination of US Patent No. 6,236,887—Official Action and IDS Considered Dated Jun. 20, 2008, U.S. Appl. No. 90/008,707.
Request for Ex Parte Reexamination of US Patent No. 6,236,887—Official Action Granting Request for Ex Parte Examination Dated Aug. 17, 2007, U.S. Appl. No. 90/008,707.
Request for Ex Parte Reexamination of US Patent No. 6,236,887 Dated Jun. 13, 2007, U.S. Appl. No. 90/008,707.
Request for Ex Parte Reexamination of US Patent No. 6,298,268—Certificate of Reexamination Issued Mar. 7, 2006, U.S. Appl. No. 90/006,788.
Request for Ex Parte Reexamination of US Patent No. 6,298,268—IDS Considered Feb. 22, 2005, U.S. Appl. No. 90/006,788.
Request for Ex Parte Reexamination of US Patent No. 6,298,268—Notice of Intent to Issue Certificate of Reexamination Dated Mar. 29, 2005, U.S. Appl. No. 90/006,788.
Request for Ex Parte Reexamination of US Patent No. 6,298,268 Dated Oct. 10, 2003, U.S. Appl. No. 90/006,788.
Request for Ex Parte Reexamination of US Patent No. 6,298,268 Order Granting Request for Ex Parte Reexamination Dated Dec. 19, 2003, U.S. Appl. No. 90/006,788.
Request for Ex Parte Reexamination of US Patent No. 6,317,631—Amendment in Response to Official Action Dated Jun. 20, 2008, Filed Aug. 20, 2008, U.S. Appl. No. 90/008,689.
Request for Ex Parte Reexamination of US Patent No. 6,317,631—IDS Dated Dec. 31, 2007, U.S. Appl. No. 90/008,689.
Request for Ex Parte Reexamination of US Patent No. 6,317,631—IDS Dated Sep. 26, 2008, U.S. Appl. No. 90/008,689.
Request for Ex Parte Reexamination of US Patent No. 6,317,631—Notice of Intent to Issue Certificate of Reexamination Dated Mar. 18, 2009, U.S. Appl. No. 90/008,689.
Request for Ex Parte Reexamination of US Patent No. 6,317,631—Official Action Dated Jun. 20, 2008, U.S. Appl. No. 90/008,689.
Request for Ex Parte Reexamination of US Patent No. 6,317,631—Order Granting Reexamination Dated Nov. 5, 2007, U.S. Appl. No. 90/008,689.
Request for Ex Parte Reexamination of US Patent No. 6,317,631—IDS Dated Jun. 8, 2007, U.S. Appl. No. 90/008,689.
Request for Ex Parte Reexamination of US Patent No. 6,330,476—Comments by 3rd Party Requestor, Response Thereto and Official Action Issued Jul. 16, 2008, U.S. Appl. No. 95/000,032.
Request for Ex Parte Reexamination of US Patent No. 6,330,476—Communication of Right to Appeal dated Jul. 16, 2008, Application No. 95 000,032.
Request for Ex Parte Reexamination of US Patent No. 6,330,476—IDS Filed May 4, 2007, U.S. Appl. No. 95/000,032.
Request for Ex Parte Reexamination of US Patent No. 6,330,476—Official Action by USPTO Issued Mar. 23, 2004, U.S. Appl. No. 95/000,032.
Request for Ex Parte Reexamination of US Patent No. 6,330,476—Order Granting Request for Reexamination Dated Mar. 23, 2004, U.S. Appl. No. 95/000,032.
Request for Ex Parte Reexamination of US Patent No. 6,330,476 Dated Dec. 31, 2003, U.S. Appl. No. 95/000,032.
Request for Ex Parte Reexamination of US Patent No. 6,463,324—Amendment in Response to Official Action Dated Aug. 1, 2007 Filed Oct. 1, 2007, U.S. Appl. No. 90/008,312.
Request for Ex Parte Reexamination of US Patent No. 6,463,324—Certificate of Reexamination Dated Apr. 29, 2008, U.S. Appl. No. 90/008,312.
Request for Ex Parte Reexamination of US Patent No. 6,463,324—Official Action—Notice of Intent to Reexamine Dated Jan. 24, 2008, U.S. Appl. No. 90/008,312.
Request for Ex Parte Reexamination of US Patent No. 6,463,324—Official Action Dated Aug. 1, 2007, U.S. Appl. No. 90/008,312.
Request for Ex Parte Reexamination of US Patent No. 6,463,324—Official Action, Interview Summary and References Considered Dated Nov. 6, 2007, U.S. Appl. No. 90/008,312.
Request for Ex Parte Reexamination of US Patent No. 6,463,324 Dated Nov. 1, 2006, U.S. Appl. No. 90/008,312.
Supplementary European Search Report and the European Search Opinion Dated Nov. 28, 2008 From the European Patent Office Re.: Application No. 05853465.2.
Translation of Office Action Dated Sep. 12, 2008 From the State Intellectual Property Office of the People's Republic of China Re.: Application No. 200480032636.9.
Adeghate et al. "Effect of Electrical Field Stimulation on Insulin and Glucagon Secretion From the Pancreas of Normal and Diabetic Rats", Hormonal Metabolism Research, 33: 281-289, 2001.
Antman et al. "Treatment of 150 Cases of Life-Threatening Digitalis Intoxication With Digoxin-Specific Fab Antibody Fragments. Final Report of A Multicenter Study", Circulation, 81(6): 1744-1752, 1990.
Bergsten et al. "Synchronous Oscillations of Cytoplasmic Ca2+ and Insulin Release in Glucose-Stimulated Pancreatic Islets", The Journal of Biological Chemistry, 269(12): 8749-8753, 1994.
Cano et al. "Dose-Dependent Reversal of Digoxin-Inhibited Activity of An In-Vitro Na+K+ATPase Model by Digoxin-Specific Antibody", Toxicology Letters, 85(2): 107-111, 1996. Abstract.
Crider et al. "2-Pyridylthioureas: Novel Nonpeptide Somatostatin Agonists With SST4 Selectivity", Current Pharmaceutical Design, 5(4): 255-263, 1999.
Davis et al. "Insulin, Oral Hypoglycemic Agents, and the Pharmacology of the Endocrine Pancreas", The Pharmacological Basis of Therapeutics, Chap.60: 1487-1499, 1507-1510.
Devedeux et al. "Uterine Electromyography: A Critical Review", American Journal of Obstetrics & Gynecology, 169(6): 1636-1653, 1993. Abstract.
Gold et al. "Evidence That Glucose 'Marks' B Cells Resulting in Preferential Release of Newly Synthesized Insulin", Science, 218(4567): 56-58, 1982. Abstract.
Gomis et al. "Oscillatory Patterns of Electrical Activity in Mouse Pancreatic Islets of Langerhans Recorded In Vivo", European Journal of Physiology, 432(3): 510-515, 1996.
Gussoni et al. "Dystrophin Expression in the MDX Mouse Restored by Stem Cell Transplantation", Nature, 401(6751): 390-394, 1999. Abstract.
Hinke et al. "Dipeptidyl Peptidase IV (DPIV/CD26) Degradation of Glucagon. Characterization of Glucagon Degradation Products and DPIV-Resistant Analogs", The Journal of Biological Chemistry, 275(6): 3827-3834, 2000.
Holst et al. "Nervous Control of Pancreatic Endocrine Secretion in Pigs. I. Insulin and Glucagon Responses to Electrical Stimulation of the Vagus Nerves", Acta Physiologica Scandinavica, 111(1): 1-7, 1981. Abstract. P.5, r-h Col., Last Line—P.6, 1-h Col., First Line.
Jaremko et al. "Advances Toward the Implantable Artificial Pancreas for Treatment of Diabetes", Diabetes Care, 21(3): 444-450, 1998.
Kurose et al. "Glucagon, Insulin and Somatostatin Secretion in Response to Sympathetic Neural Activation in Streptozotocin-Induced Diabetic Rats. A Study With the Isolated Perfused Rat Pancreas In Vitro", Diabetologia, 35: 1035-1041, 1992. Abstract.
Luiken et al. "Contraction-Induced Fatty Acid Translocase/CD36 Translocation in Rat Cardiac Myocytes Is Mediated Through AMP-Activated Protein Kinase Signaling", Diabetes, 52: 1627-1634, 2003.
Magnus et al. "Model of Beta-Cell Mitochondrial Calcium Handling and Electrical Activity. II. Mitochondrial Variables", American Journal of Physiology, Cell Physiology, 274(43): C1174-C1184, 1998.
Meurer et al. "Properties of Native and In Vitro Glycosylated Forms of the Glucogan-Like Peptide-1 Receptor Antagonist Exendin(9-39)", Metabolism, 48(6): 716-724, 1999.
Misler et al. "Electrophysiology of Stimulus-Secretion Coupling in Human B-Cells", Diabetes, 41(10): 1221-1228, 1992. Abstract.

Moran et al. "Digoxin-Specific Fab Fragments Impair Renal Function in the Rat", Journal of Pharmacy and Pharmacology, 46(10): 854-856, 1994. Abstract.

Nadal et al. "Homologous and Heterologous Asynchronicity Between Identified Alpha-, Beta- and Gamma-Cells Within Intadct Islets of Langerhans in the Mouse", Journal of Physiology, 517(Pt 1): 85-93, 1999.

Ohinata et al. "Proadrenomedullin N-Terminal 20 peptide (PAMP) elevates Blood Glucose Levels Via Bombesin Receptor in Mice", FEBS Letters, 473(2): 207-211, 2000.

Palti et al. "Islets of Langerhans Generate Wavelike Electric Activity Modulated by Glucose Concentration", Diabetes, 45: 595-601, 1996. Abstract.

Park et al. "Significant Cholinergic Role in Secreted-Stimulated Exocrine Secretion in Isolated Rat Pancreas", American Journal of Physiology, 274(2 Pt 1): G413-G418, 1998. Abstract.

Patterson et al. "Therapeutic Angiogenesis.The New Electrophysiology?", Circulation, 99: 2614-2616, 1999.

Pokrovsky et al. "Physiology of Man", Moscow Medicine, 1: 82-83, 94, 2: 42, 54, Translation of Extracts. Translation English!

Porksen et al. "Section 6: Pulsatile and Phasic Insulin Release in Normal and Diabetic Man. Pulsatile Insulin Secretion: Detection, Regulation, and Role in Diabetes", Diabetes, 51(Suppl.1): S245-S254, 2002.

Rivera et al. "Regualtion of Protein Secretion Through Controlled Aggregation in the Endoplasmic Reticulum", Science, 287: 826-830, 2000.

Schirra et al. "Exendin(9-39)Amide Is An Antagonist of Glucagon-Like Peptide-1(7-36)Amide in Humans", Journal of Clinical Investigation, 101(7): 1421-1430, 1996.

Serre et al. "Exendin-(9-39) Is An Inverse Agonist of the Murine Glucagon-Like Peptide-1 Receptor: Implications for Basal Intracellular Cyclic Adenosine 3',5'-Monophosphate Levels and B-Cells Glucose Competence", Endocrinology, 139(11): 4448-4454, 1998.

Shah et al. "Impact of Lack of Suppression of Glucagon on Glucose Tolerance in Humans", American Journal of Physiology, 277(2 Pt 1): E283-E290, 1999.

Shmit et al. "Physiology of Man", Moscow Medicine, 1: 78, Translation of Extracts, 1996. Translation in English.

Shuba et al. "Physiology of Vessel Smooth Muscles", Naukova Dumka, p.11-15, 142, Translation of Extracts, 1988. Translation in English!

Shumaik et al. "Oleander Poisoning: Treatment With Digoxin-Specific Fab Antibody Fragments", Annals of Emergency Medicine, 17(7): 732-735, 1988.

Singh et al. "Effect of Islet Hormones on Nerve-Mediated and Acetylcholine-Evoked Secretory Responses in the Isolated Pancreas of Normal and Diabetic Rats", International Journal of Molecular Medicine, 1(3): 627-634, 1998. Abstract. Abstract, P.633, Section 'Discussion'.

Soria et al. "Cytosolic Calcium Oscillations and Insulin Release in Pancreatic Islets of Langerhans", Diabetes & Metabolism, 24(1): 37-40, 1998.

Sukhorukov et al. "The Effect of Electrical Deformation Forces on the Electropermeabilization of Erythrocyte Membranes in Low- and High-Conductivity Media", The Journal of Membrane Biology, 163(3): 235-245, 1998. Abstract.

Tsong "Electroporation of Cell Membranes", Biophysical Journal, 60: 297-306, 1991.

Valdeolmillos et al. "In Vivo Synchronous Membrane Potential Oscillations in Mouse Pancreatic Beta-Cells: Lack of Co-Ordination Between Islets", Journal of Physiology, 493(1): 9-18, 1996.

Van Ripper et al. "Electrical Field Stimulation—Mediated Relaxation of A Rabbit Middle Cerebral Artery", Circulation Research, 70: 1104-1112, 1992.

Wang et al. "Islet Amyloid Polypeptide Tonally Inhibits Beta-, Alpha-, and Gamma-Cell Secretion in Isolated Rat Pancreatic Islets", American Journal of Physiology, 276(1 Pt 1): E19-E24, 1999.

West "The Endocrine Pancreas", Best and Taylor's Physiological Basis of Medical Practice, 12th Ed.(Chap.50): 754-769.

Wright et al. Structure of Fab hGR-2F6, A Competitive Antagonist of the Glucagon Receptor, Acta Crystallographica, Section D Biological Crystallography, 56(Pt 1): 573-580, 2000.

Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404, 1984.

Zhou et al. "Prevention of Action Potentials During Extracellular Electrical Stimulation of Long Duration", Journal of Cardiovascular Electrophysiology, 8: 779-789, 1997. Abstract.

Antman et al. "Treatment of 150 Cases of Life-Threatening Digitalis Intoxication With Digoxin-Specific Fab Antibody Fragments", Circulation, 81(6): 1744-1752, 1990.

Bargheer et al. "Prolongation of Monophasic Action Potential Duration and the Refractory Period in the Human Heart by Tedisamil, A New Potassium-Blocking Agent", Journal European Heart, 15(10): 1409-1414, 1994, Abstract.

Bers "Excitation Contraction Coupllng and Cardiac Contractile Force", Internal Medicine, 237(2): 17, 1991, Abstract.

Borst et al. "Coronary Artery Bypass Gratting Without Cardiopulomonary Bypass and Without Interuption of Native Coronary Flow Using A Novel Anastomosis Site Restraining Device (Octupus)", Journal of the American College of Cardiology, 27(6): 1356-1364, 1996.

Cano et al. "Dose-Dependent Reversal of Dixogin-Inhibited Activity of An In-Vitro Na+K+ATPase Model by Digoxin-Specific Antibody", Toxicology Letters, 85(2): 107-1011, 1996.

Cazeau et al. "Multisite Pacing for End-Stage Heart Failure: Early Experience", Pacing and Clinical Electrophysiology, 19(11): 1748-1757, 1996, Abstract.

Cheng et al. "Calcium Sparks: Elementary Events Underlying Excitation-Contraction Coupling in Heart Muscle", Science, 262(5134): 740-744, 1993, Abstract.

Cooper "Postextrasystolic Potention. Do We Really Know What It Means and How to Use It?", Circulation, 88: 2962-2971, 1993.

Coulton et al. "Magnetic Fields and Intracellular Calcium; Effects on Lymphocytes Exposed to Conditions for 'Cyclotron Resonance'", Phys. Med. Biol., 38: 347-360, 1993, Abstract.

Dillon "Synchronized Repolarization After Defibrillation Shocks. A Possible Component of the Defibrillation Process Demonstration by Optical Recordings in Rabbit Heart", Circulation, 85(5): 1865-1878, 1992.

Fain et al. "Improved Internal Defibrillation Efficacy With A Biphasic Waveform", American Heart Journal, 117(2): 358-364, 1989, Abstract.

Fleg et al. "Impact of Age on the Cardiovasvular Response to Dynamic Upright Exercise in Healthy Men and Women", Journal of Applied Physiologyl, 78: 890-900, 1995, Abstract.

Fleischhauer et al. "Electrical Resistances of Interstitial and Microvascular Space as Determinants of the Extracellular Electrical Field and Velocity of Propagation in Ventricular Myocardium", Circulation, 92: 587-594, 1995.

Foster et al. "Acute Hemodynamic Effects of Atrio—Biventricular Padng in Humans", The Society of Thoracic Surgeons, 59: 294-300, 1995, Abstract.

Franz "Bridging the Gap Between Basic Clinical Electrophysiology: What Can Be Learned From Monophasic Action Potential Recordings?", Journal Cardiovasc Electrophysiology, 5(8): 699-710, 1994, Abstract.

Franz "Method and Theory of Monophasic Action Potential Recording", Prog. Cardiovasc Dis, 33(6): 347-368, 1991.

Fromer et al. "Ultrarapid Subthreshold Stimulation for Termination of Atriventricular Node Reentrant Tachycardia", Journal of the American College Cardiology, 20: 879-883, 1992.

Fu et al. "System Identification of Electrically Coupled Smooth Music Cells: The Passive Electrically Coupled Smooth Muscle Cells: The Passive Electrical Properties", IEEE Transactions on Biomedical Engineering, 38(11): 1130-1140, 1991.

Gill et al. "Refractory Period Extension During Ventricular Pacing at Fibrillatory Pacing Rates", Pacing and Clinical Elctrophysiology, 20(3): 647-653, 1997, Abstract.

Ham et al. "Classification of Cardiac Arrhythmias Using Fuzzy Artmap", IEEE Transactions on Biomedical Engineering, 43(4): 425-429, 1996, Abstract.

Josephson "Clinical Cardiac Electrophysiology: Techniques and Interpertations", Lea & Febiger, 2nd Ed., 2 P., 1991.

Knisley et al. "Effect of Field Stimulation on Cellular Repolarization in Rabbit Myocardium", Circulation Research, 70: 707-715, 1991.

Knisley et al. "Prolgongation and Shortening of Action Potentials by Electrical Shocks in Frog Ventricular Muscle", American Journal of Physiology, 266(6): H2348-H2358, 1994, Abstract.

Koller et al. "Relation Between Repolarization and Refractoriness During Programmed Electrical Stimulation in the Human Right Ventricle", Circulation, 91(9): 2378-2384, 1995, Abstract.

Langberg et al. "Identification of Ventricular Tachycardia with Use of the Morphology of the Endocardial Electrogram", Circulation, 77(6): 1363-1369, 1988.

Lindstrom et al. "Intracellular Calcium Oscillations in A T-Cell Line After Exposure to Extremely-Low-Frequency Magnetic Fields with Variable Frequencies and Flux Densities", Bioelectromagnetics, 16(1): 41-47, 1995, Abstract.

Lubart et al. "Effect of Light on Calcium Transport in Bull Sperm Cells", J. Photochemical Photobiology, 14: 337-341, 1992.

Matheny et al. "Vagus Nerve Stimulation as A Method to Temporarily Slow or Arrest the Heart", Annals of Thoracic Surgery, 63(6): S28-29, 1997, Abstract.

McVeigh et al. "Noninvasive Measurement of Transmural Gradients in Myocardial Strain With MR Imaging", Radiology, 180(3): 677, 679-684, 1991.

Morse et al. "A Guide to Cardiac Pacemakers, Defibrillators and Related Products".

Nannini et al. "Muscle Recruitment With Intrafascicular Electrodes",IEEE Transactions on Biomedical Engineering, 38: 769-776, 1991, Abstract.

Pumir et al. "Control of Rotating Waves in Cardiac Muscle: Analysis of the Effect of Electric Fields", Proceedings: Biological Sciences, 257(1349): 129-134, 1994, Abstract.

Ranjan et al. "Electrical Stimulation of Cardiac Myocytes", Annals of Biomedical Engineering, 23(6): 812-821, 1995, Abstract.

Saksena et al. "Prevention of Recurrent Atrial Fibrillation With Chronic Dual-Site Right Atrial Pacing", Journal of the American College of Cardiology, 28(3): 687-694, 1996, Abstract.

Solomonow et al. "Control of Muscle Contractile Force Through Indirect High-Frequency Stimulation", Am. J. Physical Medicine, 62: 71-82, 1983.

Schwartz et al. "Exposure of Frog Hearts to CW or Amplitude-Modified VHF Fields: Selective Efflux of Calcium Ions at 16 Hz", Bioelectromagnetics, 11(4): 349-358, 1990, Abstract.

Skale et al. "Inhibition of Premature Ventricular Extrastimuli by Subthreshold Conditioning Stimuli", J. Am. Coll. Cardiol., 6: 133-140, 1985, Abstract.

Stevenson et al. "Electrophysiological Characteristics of Ventricular Tachycardia or Fibrillation in Relation to Age of Myocardial Infarction", Am. J. Cardiol., 57(6):.

Sweeny et al. "Countershock Strength-Duration Relationship for Myocardial Refractory Period Extension", Academic Emergency Medicine, 2(1): 57-62, 1995, Abstract.

Sweeny et al. "Refractory Interval After Transcardiac Shocks During Ventricular Fibrillation", Circulation, 94(11): 2947-2952, 1996.

Sweeny et al. "Ventricular Refractory Period Extension Caused by Defibrillation Shocks", Circulation, 82(3): 965-972, 1990.

Talit et al. "The Effect of External Cardiac Pacing on Stroke Volume", pace, 13(5): 598-602, 1990, Abstract.

Taniguchi et al. "Inhomogeneity of Cellular Activation Time and Vmax in Normal Myocardial Tissue Under Electrical Field Stimulation", Am. J. Physiol., 267: H694-H705, 1994, Abstract.

Thakor et al. "Effect of Varying Pacing Waveform Shapes on Propagation and Hemodynamics in the Rabbit Heart", The Americal Journal of Cardiology, 79(6A): 36-43, 1997, Abstract.

Verrier et al. "Electrophysiologic Basis for T Wave Alternans as An Index of Vulnerability to Ventricular Fibrillation", Journal of Cardiovascular Electrophysiology, 5(5): 445-461, 1994. Abstract.

Webster Design of Cardiac Pacemakers, IEEE Press, p. xi-xiii, 1995.

Windle et al. "Subthreshold Conditioning Stimuli Prolong Human Ventricular Refractoriness", Am. J. Cardiol., 57(6): 381-386, 1986, Abstract.

Wirtzfeld et al. "Physiological Pacing: Present Status and Future Developments", Pace, 10(Part I): 41-57, 1987. Abstract.

Yokoyama "The Phase of Supernormal Excitation in Relation to the Strength of Subthreshold Stimuli", Japanese HEart Journal, 17: 315-325, 1976.

Zipes et al. "Cardiac Electrophysiology—From Cell to Bedside", Saunders Co., 4th Ed., 1990.

Office Action Dated Jul. 13, 2009 From the State Intellectual Property Office of the People's Republic of China Re.: Application No. 200480027083.3 and Its Translation Into English.

Official Action Dated Jun. 1, 2009 From the US Patent and Trademark Office Re.: U.S. Appl. No. 10/039,845.

Official Action Dated Dec. 2, 2009 From the US Patent and Trademark Office Re.: U.S. Appl. No. 11/932,149.

Official Action Dated Dec. 3, 2009 From the US Patent and Trademark Office Re.: U.S. Appl. No. 11/318,845.

Official Action Dated Sep. 3, 2009 From the US Patent and Trademark Office Re.: U.S. Appl. No. 10/804,560.

Official Action Dated Dec. 4, 2009 From the US Patent and Trademark Office Re.: U.S. Appl. No. 11/884,389.

Official Action Dated Oct. 6, 2009 From the US Patent and Trademark Office Re.: U.S. Appl. No. 11/550,560.

Official Action Dated Oct. 8, 2009 From the US Patent and Trademark Office Re.: U.S. Appl. No. 10/116,201.

Official Action Dated Sep. 14, 2009 From the US Patent and Trademark Office Re.: U.S. Appl. No. 11/931,889.

Official Action Dated Aug. 18, 2009 From the US Patent and Trademark Office Re.: U.S. Appl. No. 10/570,576.

Official Action Dated Sep. 25, 2009 From the US Patent and Trademark Office Re.: U.S. Appl. No. 10/526,708.

Official Action Dated Aug. 28, 2009 From the US Patent and Trademark Office Re.: U.S. Appl. No. 11/802,685.

Official Action Dated Aug. 28, 2009 From the US Patent and Trademark Office Re.: U.S. Appl. No. 11/932,064.

Response Dated Nov. 22, 2009 to Official Action of Jun. 1, 2009 From the US Patent and Trademark Office Re.: U.S. Appl. No. 10/039,845.

Amended Request for Ex Parte Reexamination of US Patent No. 6,317,631 Dated Aug. 20, 2007 From the US Patent and Trademark Office Re.: U.S. Appl. No. 90/008,689.

Communication Pursuant to Article 94(3) EPC Dated Jan. 27, 2010 From the European Patent Office Re. Application No. 07110023.4.

Communication Pursuant to Article 94(3) EPC Dated Jan. 29, 2009 From the European Patent Office Re.: Application No. 04106247.2.

Communication Pursuant to Article 96(2) EPC Dated Mar. 2, 2007 From the European Patent Office Re.: Application No. 97929478.2.

Inter Partes Reexamination Communication of Patent US 6,330,476 Dated Sep. 4, 2007 From the US Patent and Trademark Office Re.: U.S. Appl. No. 95/000,032.

International Preliminary Report on Patentability Dated Dec. 1, 2004 From the International Preliminary Examining Authority Re.: Application No. PCT/IL03/00736.

International Preliminary Report on Patentability Dated Nov. 15, 2007 From the International Bureau of WIPO Re.: Application No. PCT/US2006/017281.

International Preliminary Report on Patentability Dated Jun. 21, 2007 From the International Bureau of WIPO Re.: Application No. 21 Jun. 2007.

International Preliminary Report on Patentability Dated Sep. 27, 2007 From the International Bureau of WIPO Re.: Application No. PCT/IL2006/000345.

International Preliminary Report on Patentability Dated Aug. 30, 2007 From the International Bureau of WIPO Re.: Application No. PCT/IL2006/000204.

International Search Report and the Written Opinion Dated May 12, 2006 From the International Searching Authority Re.: Application No. PCT/US05/44557.

International Search Report and the Written Opinion Dated Oct. 16, 2006 From the International Searching Authority Re.: Application No. PCT/US06/17281.

Notification of Reasons of Rejection Dated Sep. 29, 2008 From the Japanese Patent Office Re.: Application No. 2004-534013 and Its Translation Into English.

Office Action Dated Dec. 4, 2009 From the State Intellectual Property Office of the People's Republic of China Re.: Application No. 03824661.9 and Its Translation Into English.
Office Action Dated Nov. 7, 2008 From the State Intellectual Property Office of the People's Republic of China Re.: Application No. 03824661.9 and Its Translation Into English.
Office Action Dated Jan. 8, 2010 From the State Intellectual Property Office (SIPO) of the People's Republic of China Re.: Application No. 200480012687.5 and Its Translation Into English.
Office Action Dated May 8, 2009 From the State Intellectual Property Office of the People's Republic of China Re.: Application No. 03824661.9 and Its Translation Into English.
Office Action Dated Oct. 12, 2004 From the Israeli Patent Office Re.: Application No. 128955.
Office Action Dated Dec. 15, 2008 From the State Intellectual Property Office (SIPO) of the People's Republic of China Re.: Application No. 200480012687.5 and Its Translation Into English.
Official Action Dated Aug. 1, 2007 From the US Patent and Trademark Office Re.: U.S. Appl. No. 90/008,312.
Official Action Dated Oct. 1, 2009 From the US Patent and Trademark Office Re.: U.S. Appl. No. 10/237,263.
Official Action Dated Feb. 4, 2010 From the US Patent and Trademark Office Re.: U.S. Appl. No. 10/039,845.
Official Action Dated Jan. 5, 2010 From the US Patent and Trademark Office Re.: U.S. Appl. No. 11/802,685.
Official Action Dated Aug. 8, 2007 From the US Patent and Trademark Office Re.: U.S. Appl. No. 10/804,560.
Official Action Dated Jul. 15, 2008 From the US Patent and Trademark Office Re.: U.S. Appl. No. 10/116,201.
Official Action Dated Mar. 25, 2010 From the US Patent and Trademark Office Re.: U.S. Appl. No. 10/804,560.
Official Action Dated Jun. 26, 2008 From the US Patent and Trademark Office Re.: U.S. Appl. No. 11/536,794.
Official Action Dated Aug. 31, 2007 From the US Patent and Trademark Office Re.: U.S. Appl. No. 11/536,794.
Official Action Dated Jul. 31, 2008 From the US Patent and Trademark Office Re.: U.S. Appl. No. 11/318,845.
Request for Ex Parte Reexamination of Patent No. 6,363,279, Response to Official Action Dated Jun. 20, 2008 Submitted Aug. 20, 2008 From the US Patent and Trademark Office Re.: U.S. Appl. No. 90/008,688.
Response Dated Mar. 1, 2010 to Official Action of Aug. 28, 2009 From the US Patent and Trademark Office Re.: U.S. Appl. No. 11/932,064.
Response Dated Oct. 1, 2007 to Official Action of Aug. 1, 2007 From the US Patent and Trademark Office Re.: U.S. Appl. No. 90/008,312.
Response Dated Sep. 1, 2004 to Communication Pursuant to Article 96(2) EPC of Mar. 2, 2004 From the European Patent Office Re.: Application No. 97929478.2.
Response Dated Feb. 2, 2010 to Official Action of Dec. 2, 2009 From the US Patent and Trademark Office Re.: U.S. Appl. No. 11/932,149.
Response Dated Apr. 3, 2008 to Official Action of Jan. 3, 2008 From the US Patent and Trademark Office Re.: U.S. Appl. No. 10/116,201.
Response Dated Mar. 3, 2010 to Official Action of Sep. 3, 2009 From the US Patent and Trademark Office Re.: U.S. Appl. No. 10/804,560.
Response Dated Feb. 4, 2010 to Official Action of Dec. 4, 2009 From the US Patent and Trademark Office Re.: U.S. Appl. No. 11/884,389.
Response Dated Mar. 4, 2010 to Official Action of Nov. 5, 2010 From the US Patent and Trademark Office Re.: U.S. Appl. No. 10/549,216.
Response Dated Oct. 4, 2007 to Official Action of Sep. 4, 2007 From the US Patent and Trademark Office Re.: U.S. Appl. No. 95/000,032.
Response Dated Apr. 6, 2010 to Official Action of Oct. 6, 2009 From the US Patent and Trademark Office Re.: U.S. Appl. No. 11/550,560.
Response Dated Feb. 7, 2010 to Official Action of Dec. 2, 2009 From the US Patent and Trademark Office Re.: U.S. Appl. No. 11/932,149.
Response Dated Feb. 7, 2010 to Official Action of Nov. 3, 2009 From the US Patent and Trademark Office Re.: U.S. Appl. No. 11/931,724.
Response Dated May 7, 2007 to Examination Report of Mar. 2, 2007 From the Government of India, Patent Office Re.: Application No. 533/CHENP/2005.
Response Dated Feb. 8, 2010 to Official Action Dated Oct. 1, 2009 From the US Patent and Trademark Office Re.: U.S. Appl. No. 10/237,263.

Response Dated Feb. 9, 2010 to Official Action of Oct. 8, 2009 From the US Patent and Trademark Office Re.: U.S. Appl. No. 10/116,201.
Response Dated Mar. 15, 2010 to Official Action of Sep. 14, 2009 From the US Patent and Trademark Office Re.: U.S. Appl. No. 11/931,889.
Response Dated Jan. 17, 2008 to Official Action of Jul. 18, 2007 From the US Patent and Trademark Office Re.: U.S. Appl. No. 10/039,845.
Response Dated Feb. 18, 2010 to Official Action of Aug. 18, 2009 From the US Patent and Trademark Office Re.: U.S. Appl. No. 10/570,576.
Response Dated Apr. 20, 2006 to Communication Pursuant ot Article 96(2) EPC of Nov. 2, 2005 From the European Patent Office Re.: Application No. 97929478.2.
Response Dated Aug. 20, 2008 to Official Action of Jun. 20, 2008 From the US Patent and Trademark Office Re.: U.S. Appl. No. 90/008,689.
Response Dated May 21, 2008 to Office Action of Dec. 11, 2007 From the Japanese Patent Office Re.: Application No. 09-525055.
Response Dated Dec. 24, 2006 to Office Action of Jul. 18, 2006 From the Japanese Patent Office Re.: Application No. 10-513446.
Response Dated Dec. 25, 2006 to Notice of Reasons for Rejection of Jul. 18, 2006 From the Japanese Patent Office Re.: Application No. 09-529637.
Response Dated Jan. 25, 2007 to Examination Report of Jul. 7, 2006 From the Government of India, Patent Office Re.: Application No. 533/CHENP/2005.
Response Dated Mar. 25, 2010 to Official Action of Sep. 25, 2009 From the US Patent and Trademark Office Re.: U.S. Appl. No. 10/526,708.
Summons to Attend Oral Proceedings Pursuant to Rule 115(1) EPC Dated Dec. 22, 2008 From the European Patent Office Re.: Application No. 97929480.8.
Translation of Decision of Rejection Dated Apr. 22, 2009 From the Japanese Patent Office Re.: Application No. 2004-534013.
Translation of Notice of Reasons for Rejection Dated Jul. 18, 2006 From the Japanese Patent Office Re.: Application No. 9-529637.
Official Action Dated Mar. 31, 2010 From the US Patent and Trademark Office Re.: U.S. Appl. No. 10/237,263.
Official Action Dated Apr. 27, 2010 From the US Patent and Trademark Office Re.: U.S. Appl. No. 10/570,576.
Blank et al. "Initial Interactions in Electromagnetic Field-Induced Biosynthesis", Journal of Cellular Physiology, 199: 359-363, 2004.
Response Dated May 6, 2010 to Office Action Dated Jan. 8, 2010 From the State Intellectual Property Office (SIPO) of the People's Republic of China Re.: Application No. 200480012687.5.
Invitation Pursuant to Rule 62a(1) EPC and Rule 63(1) EPC Dated May 5, 2010 From the European Patent Office Re.: Application No. 04719312.3.
Official Action Dated May 5, 2010 From the US Patent and Trademark Office Re.: U.S. Appl. No. 11/884,389.
Official Action Dated May 26, 2010 From the US Patent and Trademark Office Re.: U.S. Appl. No. 11/318,845.
Official Action Dated Apr. 30, 2010 From the US Patent and Trademark Office Re.: U.S. Appl. No. 11/932,149.
Response Dated May 4, 2010 to Official Action of Jan. 5, 2010 From the US Patent and Trademark Office Re.: U.S. Appl. No. 11/802,685.
Translation of Notice of Reasons for Rejection Dated Apr. 27, 2010 From the Japanese Patent Office Re.: Application No. 2007-206282.
Translation of Notification of Reasons of Rejection Dated Apr. 12, 2010 From the Japanese Patent Office Re.: Application No. 2006-525265.
Official Action Dated Jun. 28, 2010 From the US Patent and Trademark Office Re.: U.S. Appl. No. 11/931,889.
Supplementary European Search Report Dated Jun. 7, 2010 From the European Patent Office Re. Application No. 04770468.9.
Official Action Dated May 21, 2010 From the US Patent and Trademark Office Re.: U.S. Appl. No. 10/116,201.
Official Action of Apr. 30, 2010 From the US Patent and Trademark Office Re.: U.S. Appl. No. 11/931,724.

Response Dated May 3, 2010 to Official Action of Dec. 3, 2009 From the US Patent and Trademark Office Re.: U.S. Appl. No. 11/318,845.

Official Action Dated Jun. 11, 2010 From the US Patent and Trademark Office Re.: U.S. Appl. No. 11/932,064.

Official Action Dated Jun. 11, 2010 From the US Patent and Trademark Office Re.: U.S. Appl. No. 11/550,560.

* cited by examiner

APPARATUS AND METHOD FOR DELIVERING ELECTRICAL SIGNALS TO MODIFY GENE EXPRESSION IN CARDIAC TISSUE

RELATED APPLICATIONS

The present application is a US National Phase of PCT Application No. PCT/US2004/007589, filed on Mar. 10, 2004, published as WO 2004/080533. This application is based upon and claims the benefit under 35 USC 119(e) of U.S. provisional patent application Ser. No. 60/453,349, filed Mar. 10, 2003, and U.S. provisional patent application Ser. No. 60/503,075, filed Sep. 15, 2003, the disclosures of which are incorporated herein by reference in their entirety.

FIELD OF THE INVENTION

The present invention is related to the field of cardiac muscle control. In some embodiments, the invention relates to the use of electrical signals to treat heart failure and/or other diseases, by modification of gene expression.

BACKGROUND OF THE INVENTION

Heart Failure affects (and/or is possibly caused by) several mechanisms that are involved in the heart functioning. Among those mechanisms the expression of some genes may be affected to a depressed or over expressed condition, which affects the normal functioning of the cells and the muscle as a whole. The expression of several genes is also used as a clinical marker for the progression of the disease.

Within the literature dealing with changes in gene expression and proteins associated with heart failure, one could find changes in mRNA gene expression of brain and atrial natriuatic peptides (BNP, ANP), basic fibroblast growth factor (bFGF), mRNA gene expression for alfa myosin heavy chain aMHC, and gap junction protein connexin 43. Plasma levels of brain (B-Type) and atrial (A-Type) natriuretic peptides are increased in heart failure (HF) and are predictive of poor outcome. Increased levels of basic fibroblast growth factor (bFGF) is associated with increased angiogenesis, with increased capillary density, and with improved left ventricular (LV) ejection fraction (as demonstrated also in dogs with heart failure). Myosin heavy chain (MHC) is a key component of the cardiac contractile machinery. Recent studies showed that a switch from the aMHC to the βMHC isoform occurs in patients with heart failure. This switch may partly contribute to the progressive deterioration of left ventricular function characteristic of heart failure.

Loss of gap junctions and impaired intracellular communications are characteristic features of remodeling in heart failure and result from rapid loss of the gap junction protein connexin 43. Loss of connexin 43 has also been reported to result in malignant ventricular arrhythmias in patients with heart failure.

It has previously been shown that in dogs with heart failure, delivery of non-excitatory cardiac contractility modulation (CCM) electrical signals to left ventricular muscle during the absolute refractory period leads to chronic improvement in left ventricular function and remodeling. In patients and dogs with heart failure, chronic CCM therapy was also associated with suppression of ventricular arrhythmias.

Excitable tissue control (ETC) devices are devices which modulate the activity of excitable tissues by application of non-excitatory cardiac contractility modulation (CCM) electrical field signals to the excitable tissue through suitable electrodes in contact with the tissue. For example, ETC devices may be used, inter alia, to increase or decrease the contractility of cardiac muscle in vitro, in vivo and in situ, as disclosed in detail in PCT application No. PCT/IL97/00012 (International Publication No. WO 97/25098) to Ben-Haim et al., titled "ELECTRICAL MUSCLE CONTROLLER" and U.S. Pat. No. 6,317,631, the disclosures of both of which are incorporated herein in their entirety by reference.

OBJECTS OF THE INVENTION

It is an object of some embodiments of the invention to provide a method and device for cardiac muscle control.

It is an object of some embodiments of the invention to provide non-excitatory or non-excitatory and excitatory cardiac contractility modulation signals to affect the heart such as to treat arrhythmias.

It is an object of some embodiments of the invention to provide non-excitatory or non-excitatory and excitatory cardiac contractility modulation signals to affect the heart such as to enable improved contraction of the heart muscle.

It is an object of some embodiments of the invention to provide a method and apparatus for delivering non-excitatory or non-excitatory and excitatory cardiac contractility modulation signals to modify gene expression and protein levels associated with the functioning of the heart to improve cardiac function.

It is an object of some embodiments of the invention to provide a method and apparatus to treat heart failure by modifying the expression of genes associated with the excitable heart tissue.

These and other objects of embodiments of the invention will become more apparent in the discussion below.

SUMMARY OF THE INVENTION

According to some embodiments of the present invention non-excitatory signals such as cardiac contractility modulation signals, or non-excitatory and excitatory signals delivered to cardiac tissue of a failing heart for several hours or longer or shorter periods of time, change the expression of several genes that effect the cardiovascular system function. The changes in the expression improve cardiac function and may lead to reversal of the progression of heart failure disease or even return the heart to more normal functioning.

As reflected in the experimental evidence discussed below, CCM signal delivery causes improvement in cell and muscle activity as evidenced by mRNA expression. More specifically, CCM signals reduce the mRNA gene expression of brain and atrial natriuatic peptides (BNP, ANP), increase levels of basic fibroblast growth factor (bFGF), and normalize mRNA gene expression for alfa myosin heavy chain aMHC.

Plasma levels of brain (B-Type) and atrial (A-Type) natriuretic peptides are increased in heart failure (HF) and are predictive of poor outcome. According to certain embodiments of the invention CCM therapy reduces mRNA gene expression of both B-Type and A-Type natriuretic peptides.

Increased levels of basic fibroblast growth factor (bFGF) are associated with increased angiogenesis. It was previously shown that increased mRNA gene expression of bFGF is associated with increased capillary density in dogs with chronic heart failure. It was also shown that an increase in capillary density is associated with improved left ventricular ejection fraction, for example, in dogs with heart failure. According to certain embodiments of the invention CCM therapy restores mRNA gene expression for bFGF to above normal level or above diseased levels. CCM therapy appears to enhance expression of bFGF and, as such, may be a therapeutic modality that enhances angiogenesis, a condition that is likely to be important in the treatment of chronic heart failure and possibly angina pectoris.

Myosin heavy chain (MHC) is a key component of the cardiac contractile machinery. Recent studies showed that a switch from the aMHC to the βMHC isoform occurs in patients with heart failure. This switch may partly contribute to the progressive deterioration of LV function characteristic of heart failure. According to certain embodiments of the invention CCM therapy improves mRNA gene expression for aMHC and may bring it to levels which are considered substantially normal. Since aMHC is associated with faster velocity of shortening of cardiac muscle compared to the slow-contracting βMHC, this normalization may be responsible, in part, for the observed improvement of LV EF after CCM therapy and can be used for the treatment of heart failure in patients.

Since CCM signals may be used to reduce mRNA gene expression of both B-Type and A-Type natriuretic peptides, restore mRNA gene expression for bFGF to above normal level and/or normalize mRNA gene expression for aMHC, this therapy may be used to improve cardiac function and may be used as a therapeutic modality that enhances angiogenesis, a condition that is likely to important in the treatment of chronic heart failure and possibly angina pectoris.

Moreover, since aMHC is associated with faster velocity of shortening of cardiac muscle as compared to the slow-contracting βMHC, treating the failing heart by means of CCM delivery aimed to improve, or to normalize, ANP and BNP levels may be used to attain better contraction, and may be responsible, in part, for the observed improvement of LV EF after CCM therapy.

According to some embodiments of the invention, the non-excitatory cardiac contractility signals are used for treatment of arrhythmias and/or improvement of interacardiac connections between the cells by promoting the expression of associated genes and, in particular, the connexin 43 protein that is a contributor to the creation of the gap junction between the cells. This may be used to achieve improved contraction and/or synchronization of the ventricles. Improved contraction of the left ventricle can improve the synchronicity of the contraction and increase cardiac contractility and may also alleviate a patient's suffering from heart failure.

While some particular examples of genes are shown to have their expression modified, it is expected that other genes have their expression modified as well. In an exemplary embodiment of the invention, the effect of applying a CCM signal is to improve the expression profile of some of the cardiac cells to be healthier and/or better suited for their functioning.

In some embodiments of the invention non-excitatory fields are applied which do not have a clinically significant cardiac contractility modification effect.

In an exemplary embodiment of the invention, a device is used to apply a CCM signal and the effects on gene expression are monitored, so that application of the CCM or other non-excitatory signal can be modified. Optionally, CCM application is stopped when a desired gene expression effect is achieved. Optionally, CCM parameters are optimized for a particular patient or disease state. Optionally, the device includes a closed loop which sensing the gene expression effect of the CCM signal and modifies it accordingly.

There is thus provided in accordance with an exemplary embodiment of the invention, a device capable of delivering non-excitatory or non-excitatory and excitatory signals to heart tissue that will modify gene expression of cells in the heart tissue in a way to improve the cardiac function.

There is also provided in accordance with an exemplary embodiment of the invention, a device capable of delivering non-excitatory cardiac contractility or non-excitatory and excitatory modulation signals to heart tissue that will modify the expression of BNP and ANP in the heart tissue for treatment of heart failure.

There is also provided in accordance with an exemplary embodiment of the invention, a device capable of delivering non-excitatory or non-excitatory and excitatory cardiac contractility modulation signals to heart tissue that will normalize or better the expression of alfa myosin heavy chain aMHC in the heart tissue for treatment of heart failure.

There is also provided in accordance with an exemplary embodiment of the invention, a device capable of delivering non-excitatory or non-excitatory and excitatory cardiac contractility modulation signals that will modify the expression of basic fibroblast growth factor (bFGF) in the heart tissue for treatment of heart failure.

There is also provided in accordance with an exemplary embodiment of the invention, a method for improving heart function by modifying the expression in heart tissue of genes that effect cardiovascular system function.

There is also provided in accordance with an exemplary embodiment of the invention, a method for treating heart failure by modifying the expression in heart tissue of genes that effect cardiovascular system function. Optionally, the heart failure is congestive heart failure. Alternatively or additionally, the non-excitatory or non-excitatory and excitatory cardiac contractility modulation signals are delivered to heart tissue to modify gene expression in the heart tissue. Optionally, the signal or signals reduce mRNA gene expression of BNP, ANP, or both BNP and ANP. Optionally, the signal or signals restore mRNA gene expression for bFGF to above normal level. Optionally, there is also provided in accordance with an exemplary embodiment of the invention, a the signal or signals normalize or better nRNA gene expression for aMHC.

There is also provided in accordance with an exemplary embodiment of the invention, a method of treating a patient with a cardiac related disease, comprising:
determining a desired gene expression profile in cardiac tissue; and
applying a non-excitatory signal to the cardiac tissue to achieve the desired gene expression profile.

There is also provided in accordance with an exemplary embodiment of the invention, a device adapted to apply a non-excitatory field to a heart, characterized in that the device is adapted to take an effect on gene expression into account in its functioning. Optionally, said device is implantable. Alternatively or additionally, said device includes a feedback control loop which modifies an application of non-excitatory field in response to an indication of a gene expression effect of a previous application of a non-excitatory field. Optionally, said device includes a watchdog which stops or modifies application of an electrical signal to a heart responsive to an effect of such application on gene expression in the heart.

DETAILED DESCRIPTION OF THE INVENTION

Figure 1:
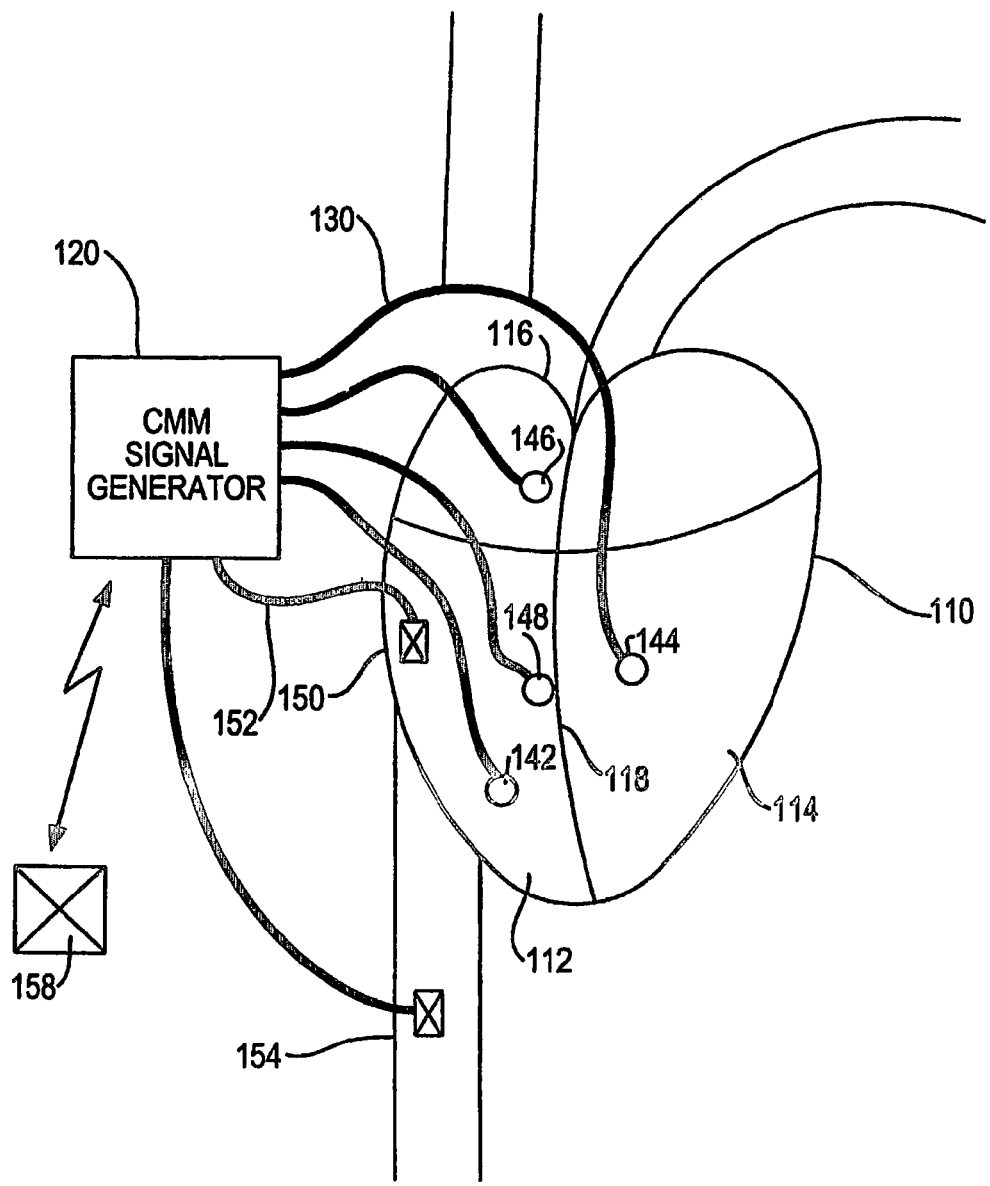
FIG. 1 is a schematic representation of an apparatus useful to deliver electrical signals according to an exemplary embodiment of the invention.

According to some embodiments of the invention, non-excitatory or non-excitatory and excitatory CCM signals are applied to cardiac tissue in a patient's heart. The signals applied may be either completely non-excitatory or a mixture of non-excitatory and excitatory signals. The signals may be superpositioned, or may be applied intermittently, for example, in a ratio of from about 20:1 to about 1:10, or in a ratio of from about 10:1 to about 1:1, for example, based upon the respective voltages. The signals may each have a frequency, for example, from about 0.1 Hz to about 1000 H. In another example, one may use signal frequencies in the range of from about 10 to about 80 Hz. The signals may each have a voltage of from about 10 mV to about 50 V. In another example, one may limit the voltage to the range of from about 1 to about 15 V, or even further limit to use voltage in the range of from about 3 to about 10 V. In another example, the signals may be delivered in synchronization with the heart activity, in a configurable delay and duration from local muscle activity. For example, it is possible to apply signals in a delay of up to 150 msec from local electrical activity detection. The delay may further be limited to up to 100 msec. In another example, one may apply the signals in a duration of up to 150 msec. It is possible to limit the range even further to use a duration of up to 50 msec, for example, about 10 msec, about 20 msec, about 30 msec or about 40 msec. In another example one may use a signal duration which is longer than 3 times the chronaxie, or even longer than 5 msec. In another example, one may use a signal duration which is longer than 8 msec, for example, 20 msec or 40 msec.

Optionally, the signal has a balanced waveform, for example, being in the shape of a byphasic pulse.

The time duration of application of a CCM therapy can vary greatly. It could be, for example, 10 minutes, 1 hour, 2 hours, 6 hours, a day, a week, or a month. One or more break periods and/or periods of rest to test the chronic effect of the signal may be provided, for example, to test if a gene expression remains altered even after a week without CCM application. It should also be appreciated that gene expressions levels may change over times. For example, a cell with missing connexin 43 may respond to a CCM signal by significant expression of connexin 43 mRNA fragments and, once its needs are met, reduce such expression. An improvement in cell function may be immediate or may be delayed and/or gradual and/or dependent on other factors. In any case, such changes in gene expression caused by lack of need of a cell are optionally taken into account when measuring positive effect of the CCM signal. Optionally, cells are periodically rested so that they can be pumped for more generation of desired secretions and/or proteins.

In an exemplary embodiment of the current invention, CCM signals are set to a voltage of 3-7.5 Volts, train of 1-5 biphasic pulses delivered every beat, all together with a duration of 10-80 msec, with a delay from local electrical activity of up to 100 msec. It is expected that other pulse parameters will be able to produce a desired gene expression effect.

In a preferred embodiment, the signal is delivered during the absolute refractory period of the local tissue, where the parameters are tuned to produce a desired gene expression effect. In yet another embodiment, the signal includes pacing, followed by a non-excitatory signal where the parameters provide a desired gene expression effect. In yet another embodiment, the signal is a prolonged pacing signal, having the a first excitatory edge, continued by a signal longer than 5 msec, where the parameters are tuned to produce a desired gene expression effect.

In an exemplary embodiment of the invention, the non-excitatory and/or the excitatory signals will be generated by a signal generator unit, whether implanted or external. The device may comprise a sensor of cardiac activity, and may comprise additional sensors and/or inputs from other sensors, associated directly or indirectly with the levels of relevant gene expression, to enable tuning of the signal delivery such as to achieve desired change in the measured parameters.

Exemplary Implementation

FIG. 1 describes an exemplary embodiment of the present invention. A CCM signal generator unit 120 is connected to a heart 110 with leads 130 and one or more electrodes 142-148. Electrodes 142, 144, 146, 148 may be located, for example, in various locations such as right ventricle 112, left ventricle 114, atria 116 or septum 118, respectively, whether through endocardial, epicardial or intravenous approach. The electrodes and leads are optionally used to sense cardiac activity from one or more locations and may be used to deliver CCM signals to one or more locations. CCM signal generator unit 120 may receive input measured from various sensors. For example, one or more such sensors 150 may be attached to the heart (whether inside or outside). In additional example, one or more such sensors 154 may be located in blood vessels, or in another body organ. Such sensors may be directly connected via connectors 152 to convey the measured signal to the CCM signal generator unit 120. In an additional example, unit 120 may receive input measured by sensors 158 which are not directly connected to the unit 120, for example, by external sensors with, for example, wireless connection. Such sensors may be used to measure the levels of various biochemical compounds, including, for example, levels of mRNA, proteins, peptides, etc. These sensors may be made of commercially available technologies of bio-chips used for analysis of compounds in biological specimens (for example, bio-chips by Affymetrix, Inc. for DNA analysis). The CCM signal generator may receive the signals from the sensors or may be tuned according to such readings, and may receive signals related to cardiac activity to determine parameters and deliver the CCM signals, such as to affect the levels of relevant gene expression and relevant proteins. Optionally, generator (device 120) includes a limited number of biochemical testing cells, each of which is selectively activated when a state of gene expression is to be determined. Such miniaturized genomic and biochemical systems are known in the art. For example, a blood inlet with 10 cells for testing blood may be provided. In another example, a tube is provided with an inner screw element for removing a tissue sample and conveying it to a testing chamber in the device. Alternatively, an external control unit is provided, for example, to which test results or tissue biopsies is provided. this external control unit decides on changes and/or receives input form a human user.

Figure 2:
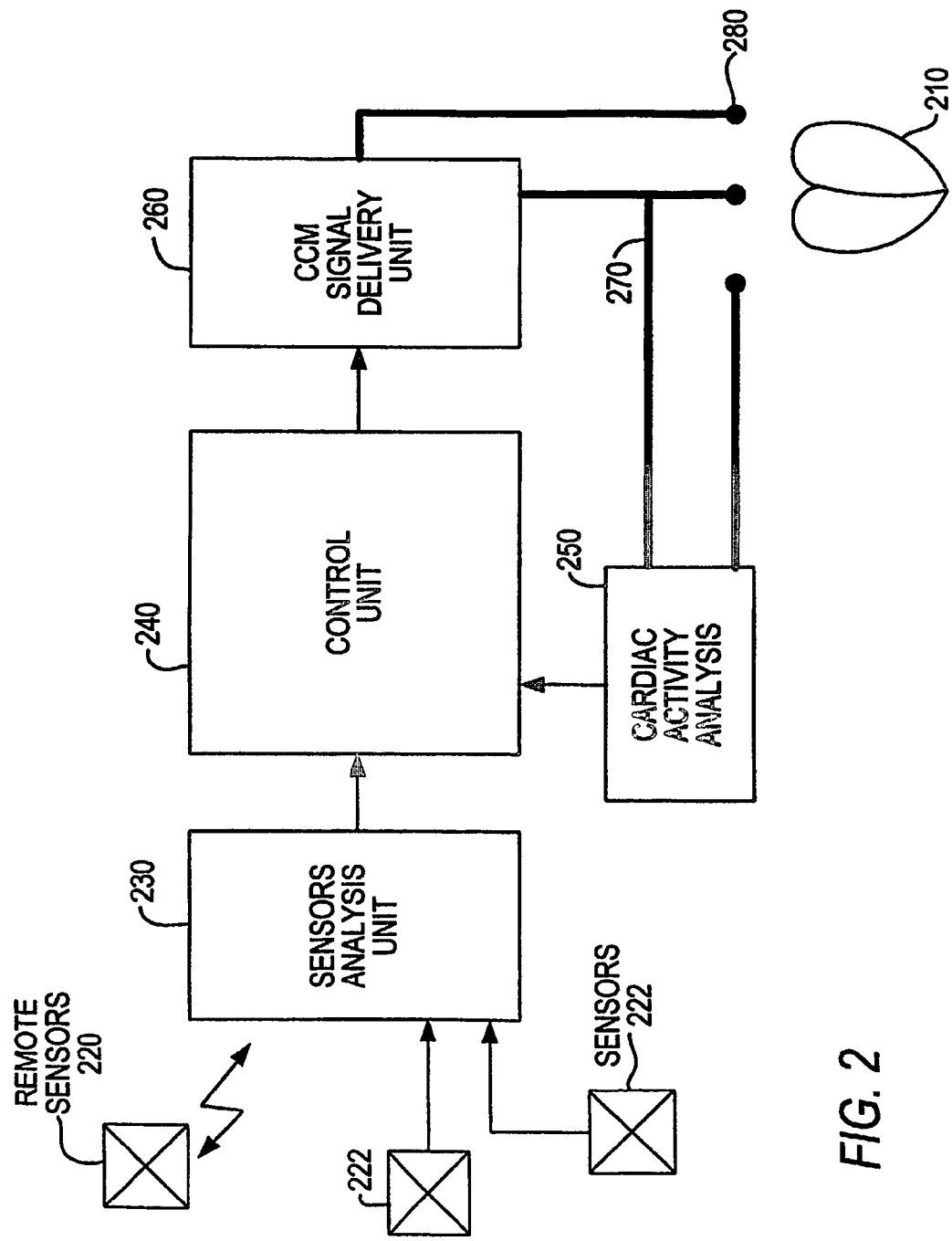
FIG. 2 is a more detailed schematic representation of an apparatus useful to deliver electrical signals according to an exemplary embodiment of the invention.

FIG. 2 describes an example of a system that may be used for CCM signal generation to control levels of proteins and gene expression. The system may be comprised of sensors 222, and may receive information from remote sensors 220. The system may comprise a sensor analysis unit 230 that process the input signals. The system may further be comprised of a cardiac activity analysis unit 250, that may be used to process information received from one or more electrodes 270 attached to the heart. The system may comprise a control unit 240 that determines the parameters of the CCM signals to be delivered according to the desired treatment, and may take into account analyzed information from the sensors and cardiac activity (units 230 and 250, respectively). The system comprises of a CCM delivery unit 260 that incorporates the necessary electrical circuitry to produce the desired CCM signals. These signals are delivered to one or more of electrodes 270 and 280, to affect the levels of relevant gene expression and relevant proteins.

In one exemplary use, device 120 is tuned during implantation (or a follow-up period) to achieve a best effect as measured by gene expression. In another exemplary usage device 120 can modify its generation of CCM signals responsive to changes in the measured gene expression. It is noted that some of the sensors described herein can be used for closed loop control of device 120. Optionally, human interaction is accepted or requested. A standard type telemetry unit, for example, may be used. Such telemetry may be used, for example, for data logging, for programming and/or for real-time or off-line parameter control. It is appreciated that it is not always possible, or practical, or necessary, to achieve optimal CCM signal parameters. For example, for reasons of safety, power limitations, physiological limitations, electrode placement, time to optimize, or the like, a pulse with suboptimal parameters may be sufficient to achieve a useful therapeutic signal.

In an exemplary embodiment of the invention, device 120 is an implanted device used for relatively longer term treatment, for example, over one week, over one month, for several months or permanently. In an alternative embodiment of the invention, device 120 is an external device, for example, with implanted leads. Alternatively, an electric field for the CCM is applied from outside the body. External devices may be useful, for example, for patients which show a gene expression response after a short treatment (e.g., 1 hour or less, a day), or for acute use (e.g., temporary heart failure). Depending on the patient, a desired or suitable gene expression modification may be achieved by application of CCM at various periodicies, for example, once a minute, once an hour, once a day, once a week or less or more often. As described below, CCM may also be provided on demand in response to its effect, for example, when a gene expression profile reaches a certain threshold. In some situations, CCM may be applied acutely, for example, using a catheter, for example, during surgery or as a stand-alone treatment.

Though the mechanism of action is yet to be explored and without limiting the actual application, one may theorize that the electrical current modulates ion availability to organelles which availability modulation affects biochemical reactions and/or directly affects gene transcription. Another possible explanation is that the signal induces mechanical and electrical functionality of the tissue, which alleviates stress on the cells thus eliminates the triggers for irregular genes. Alternatively, such induces functionality may in itself cause, trigger or modulate certain gene transcription. Possibly, any signal which improves the functioning of the cells and/or reduces stress on them and/or increases (or decrease) plateau durations and/or calcium availability inside the cells or organelles thereof, may have a utilizable gene transcription and/or expression effect.

It is further another preferred embodiment of the current invention to include in the device inputs from biochemical sensors, whether incorporated in the device or connected to the device, reporting the levels of the desired analyst. In yet another preferred embodiment, the changes in level of expression are indirectly deduced from indirect measurements, including electrical or mechanical sensors (e.g., arrhythmia changes or contraction force) related to the activity of the analysts. Optionally, a chronic change in contractility, for example, is correlated with changes in gene expression. Thus, changes in gene expression of various genes may be deduced (in one patient or in a group of patients) from changes in electrical and mechanical behavior of the heart or other body systems (e.g., measuring fluid retention). In some implementations one of the genes described here is detected as a marker for indicating that other genes are having their expression modified and/or as an indicator of a particular gene expression profile. Alternatively, a different gene may be used as a marker or indicator for the genes described herein or for other genes.

Various design making methods may be applied for stopping, starting or modifying CCM signal application and parameters. In one example, device 120 changes CCM delivery based on measured levels, based on a pre-programmed decision rules. Alternatively or additionally, device 120 applies a CCM signal or signal series whenever the analyst level cross a threshold. Alternatively or additionally, device 120 applies the signal when a calculation combining multiple parameters crosses a threshold. Alternatively or additionally, the signal parameters (delay duration, frequency, voltage, polarity, pulse train, signal shape) are changes such as to achieve the desired levels to the measured parameters. Alternatively or additionally, a negative rule is applied, for example, not applying an excitatory or non-excitatory signal that has a negative effect on gene expression.

The protocol for the actual delivery and/or implantation of wires to deliver the signals is set forth in the aforementioned PCT publication No. WO 97/25098 and U.S. Pat. No. 6,317, 631, both of which are incorporated herein by reference in their entirety. Following is a list of patents and publications which describe apparatus and methods which may be useful in conjunction with the present invention, the disclosures of all of which are incorporated herein by reference:

Cardiac output enhanced pacemaker, U.S. Pat. No. 6,463, 324, Apparatus And Method For Controlling The Contractility Of Muscles, U.S. Pat. No. 6,233,484, Controlling Heart Performance Using A Non-Excitatory Electric Field, U.S. Pat. No. 6,317,631, Muscle Contraction Assist Device, U.S. Pat. No. 6,285,906, Modulation Of Intracellular Calcium Concentration Using Non-Excitatory Electrical Signals Applied To The Tissue, PCT WO01/24871 and PCT WO00/ 12525, Electrical Muscle Controller, U.S. Pat. No. 6,363,279, Electrical Muscle Controller using a Non-Excitatory Field, U.S. Pat. No. 6,330,476, Cardiac Output Controller, U.S. Pat. No. 6,298,268, Cardiac Output Enhanced Pacemaker, U.S. Pat. No. 6,463,324, Sensor Based Regulation of Excitable Tissue Control of the Heart, WO00/27475, Regulation of Excitable Tissue Control of the Heart based on Physiological Input, WO00/27476, Trigger Based Regulation of Excitable Tissue Control of the Heart, U.S. Pat. No. 6,587,721, Pacing with Hemodynamic Enhancement, PCT IL99/00392, ETC Delivery via RV Septum, PCT WO0182771A3, Anti-Arrhythmia Device having Cardiac Contractility Modulation Capabilities, PCT WO01/30445, and Anti-Arrhythmic Device & a Method for Delivering Anti-Arrhythmic Cardiac Therapy, PCT WO01/30139.

Exemplary Treatment Method

Figure 3:
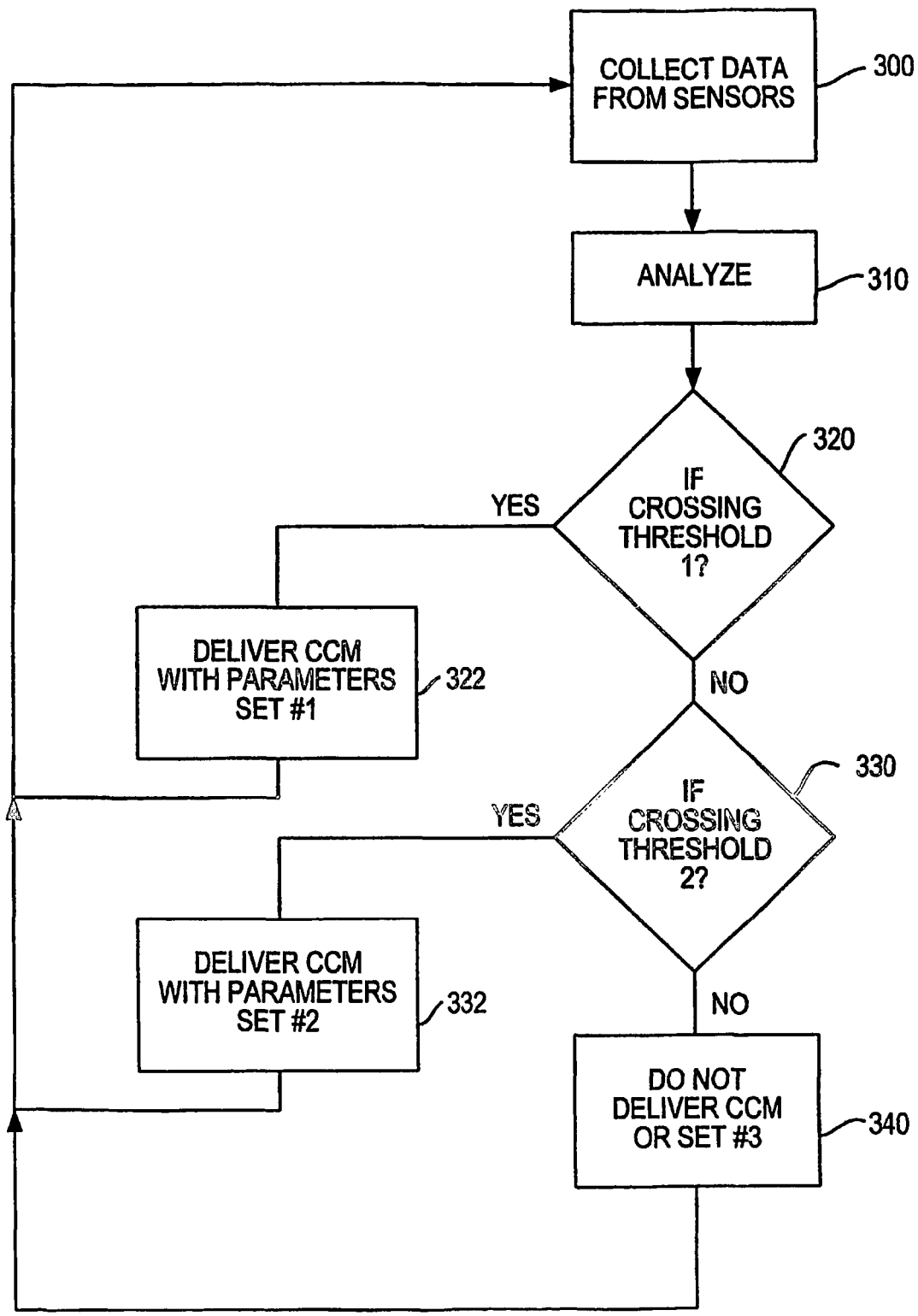
FIG. 3 is a flow chart representing a method of treating a patient for heart failure according to an exemplary embodiment of the invention.

FIG. 3 is an exemplary flowchart representing a method for treating a patient. Data is collected (300) from various sensors measuring the levels of gene expression and/or proteins. The input data may be further analyzed (310) by signal conditioning, statistical tools, classification, or other mathematical methods that produce informative result. The collected data and/or the results of analysis may be further compared (320) with a first set of thresholds to determine if CCM should be applied (322) according to a first set of parameters. If the criteria is not met, additional comparison (330) to a second set of threshold may be used to determine if CCM should be applied (332) according to a second set of parameters. Additional sets of thresholds and parameters may be used as well. If none of the criteria is met, a default set of CCM parameters may be used, or CCM may be not delivered at all. The different CCM sets may represent, for example, different power levels or different stress levels on the heart (for which reason limits on their use may be desirable)

Treatments

As will be seen form the examples below, the effects of gene expression modification can be short term or long term. For example, connexin proteins stay in the cell and modify its behavior. BFGF is an example of a material which exits the cell. However, it may have a long term effect by promoting angiogenesis.

In an exemplary embodiment of the invention, CCM signals are applied to achieve a particular beneficial effect, which is optionally monitored and/or managed by device 120.

In an example of angiogenesis promotion, device 120 is optionally positioned to electrify cardiac cells upstream of an area in need of angiogenesis.

In an exemplary embodiment of the invention, for angiogenesis, CCM is applied until a sufficient amount of angiogenesis promoting materials are secreted. Optionally, additional treatments which are expected to promote angiogenesis are provided at a same time, for example, exercise or drug treatments.

Optionally, the duration (e.g., minutes, hours, days, months) of a therapy may be determined according to the severity of a disease, as indicated by the levels of the relevant gene expressions and/or other physiological or biochemical indicators, such as those known in the art. Alternatively or additionally, other parameters, such as intensity may be set according to disease parameters.

In an example of treating or assisting arrhythmias, a CCM signal is optionally applied (e.g., continuously or periodically) to a cardiac muscle section until a desired improvement in conduction velocity is achieved. For example, in atrial fibrillation, a CCM signal may be applied to all or part of an atria. Optionally, conduction velocity is modeled, for example, by reducing activity of some muscle sections, possibly preventing the effect of a CCM signal. Alternatively or additionally, some signals may be found to have a negative effect on gene expression. However, such negative effect may be utilized for modeling muscle mass and/or conduction velocity in a heart. Exemplary arrhythmias other than atrial fibrillation includes, PVC, VT, heart block and ventricular de-synchronization. It is believed that some or all of these conditions may be improved by selective or non-selective enhancement of gene expression in portions of the heart.

Other conditions may also be treated. It is noted that the results of cardiac gene expression may be found outside the heart, for example, directly, such as in preventing fluid retention (e.g., by direct action of a secreted material on the kidneys) or indirectly (e.g., reversing symptoms of CHF, or reducing pain of angina pectoris.

An interaction may be found between certain drugs and CCM effects on gene expression. In an exemplary embodiment of the invention, drug dosage is changed and/or drugs stopped as a result of CCM effect on gene expression. Alternatively or additionally, some drugs may be stopped, for example, if they are found to prevent the effect of CCM (for example, possibly calcium channel blockers) on cardiac tissue or if the combination is pro-arrhythmic. Other drugs may be found to have a synergistic effect. Optionally, such drugs may be typically applied to parts of the heart to selectively prevent or enhance the effect of CCM. Optionally, CCM gene expression modification is used to enhance the activity of a drug or to overcome its negative effects (e.g., conduction velocity reduction for some anti-arrhythmia drugs).

Treatment Variations

Some variations on applying CCM signals to achieve gene expression are now described. In one variation, CCM signals are applied (e.g., continuously or periodically) until a gene expression improvement is stable. Possibly, periodic follow-up testing and/or CCM application may be needed.

In an exemplary embodiment of the invention, device 120 is used to determine in a particular patient parameters for gene expression modification. For example, device 120 is used to determine a minimum or optimum length of CCM signal application series which has a desired gene expression effect. This may be useful is reducing power requirements. Other exemplary parameters which can be thus determined are a repetition frequency of CCM and a power level of CCM. It should be noted that a CCM signal can have a gene expression effect even if little or no acute clinical contractility improvement is found directly from a beat-to-beat application of CCM.

Optionally, device 120 is used to experiment on a patient to determine parameters which are optimal for that patient. Alternatively or additionally, parameters which adversely affect gene expression are also found.

It should be noted that a there may be multiple suitable/healthy/allowable gene expression profiles. A device 120 can, for example, aim for one of these profiles and/or aim to avoid one or more known bad expression profiles and/or certain low or high gene expression values for particular genes. Optionally, a target gene expression profile or thresholds for various genes, are found by sampling large populations and/or by sampling healthy cells in the same patient. It is also noted that an optimal gene expression profile may vary between ages, races, genomic profiles, diseases, functional activity of a cell (e.g., including workload), and locations in the heart.

In some cases, gene expression values naturally fluctuate. Device 120 (or other feedback means, such as a person) optionally take these fluctuations in to account, for example, by averaging. Alternatively or additionally, these fluctuations are intentionally aimed for by cyclically stimulating and not stimulating a cell so that gene expression profiles can fluctuate more like a healthy cell.

In an exemplary embodiment of the invention, device 120 is used to map a patient's response of gene expression (or study a group of patients) to various CCM sequences and/or other parameters.

In an exemplary embodiment of the invention, device 120 or a user monitor negative effects on gene expression of certain pacing sequences and protocols and/or certain non-excitatory sequences, for example, "fencing" sequences. This may be used to limit the application of such sequences and/or to counteract their effect by a gene expression promoting signal. Possibly, a pacing regime may be found to have a beneficial effect in a certain patient, disease state and/or group of patients and thus be deemed desirable.

Optionally, gene expression monitoring is used as a safety feature in standard-type pacemakers, to indicate if a negative effect is being caused to a heart. Optionally, the gene expression effect is determined by periodically measuring the sensitivity of cardiac tissue to a CCM signal. Changes in the sensitivity are expected to be correlated, in some patients and in some cases to changes in gene expression. For example, conduction velocity might change markedly in tissue where conduction velocity was not impaired. In another example, fluid retention will either be improved or not based on whether tissue can generate additional suitable secretions. A baseline is optionally collected for patients before such use.

Another optional safety feature is tracking the heart to see abnormal ECG signals or an increase in various danger signals, like ST variability. Such variations may indicate that the changes in gene expression are not beneficial, and should be stopped, slowed down and/or supplemented by excitatory or non-excitatory signals which protect the heart and/or counteract such negative effects.

Alternatively or additionally, to stopping or modifying CCM application, an alert may be generated to a user, a physician or a caretaker.

In an exemplary embodiment of the invention, the application of standard CCM or other non-excitatory signals is modified to take into account the combination acute effects of a CCM signal and chronic effect caused by gene expression changes. For example, a degree of contractility enhancement and/or a timing may be changed to take into account changes in conduction. Optionally, a database is generated in which is stored the expected effect and/or progression of effect of a CCM signal on gene expression and the resulting changes in CCM application.

In an exemplary embodiment of the invention, prior to implantation or programming of an implanted device, a patient is tested to see if certain known CCM sequences have a desired gene expression effect and/or the degree of the effect. If the effect is small or negative, that patient may be contra-indicated for implantation. Alternatively, the results of such testing are used to classify the patients into groups of known patient types having known (e.g., previously collected) genomic or other responses to CCM signals. Optionally, non-genomic indicators, such as contractility modification are correlated with the gene expression effect. Thus, one effect can be used to predict one or more properties of the other effect.

In an exemplary embodiment of the invention, CCM is applied to achieve a numerical change in gene expression statistics. For example, an increase of 10%, 30%, 70%, 100%, 300% or any smaller, intermediate or greater percentage in the expression of a gene may be desirable. Optionally, what is desired is a reduction in expression of a gene, for example, by 20%, 50%, 80%, 90% or an intermediate or greater percentage. In some cases, a reduction (or increase) in any of a set of genes that are linked in a pathway is desired, for example, using the percentages above. In some embodiments, what is desired is an increase in volume of a secretion over time, or an absolute secretion amount or a secretion rate. For example, an increase of 20%, 50%, 200%, 1000% or a smaller, intermediate or greater amount may be a target. In some embodiments, a target is approaching a normal value, for example, halving the difference between current expression levels. In some embodiments, what is desired to make an expression profile similar to a base line, for example, differing by less than 50%, 30% or 20% from a baseline expression profile, over a set of 1, 3, 5, 10 or other number of genes or mRNA fragments.

It should be appreciated that the term "genes" was used in a general sense. However, a target may be expressed in the above numbers of a measurable quantity, such as mRNA fragments, peptides and serum analyts.

EXAMPLES

Results of three studies are presented below to demonstrate, in a non-limiting manner, the basis for the use of non-excitatory signals for changing the levels of expression of three different types of genes and by this provide therapy for heart failure:

Example 1

In one study, we examined whether four hours of continuous therapy with cardiac contractility modulation (CCM) signals from an OPTIMIZER-II ETC device (available from Impulse Dynamics) normalizes gene expression of A-Type and B-Type natriuretic peptides in LV myocardium of dogs with BF induced by coronary microembolizations. CCM leads were implanted on the anterior surface of the LV in an open chest preparation.

Signal parameters used were: CCM voltage of 3-7.5 Volts, train of 2-4 biphasic pulses delivered every beat, all together with a duration of 20-35 msec, with a delay from local electrical activity of up to 100 msec. We expect other pulse parameters to achieve the result as well, though these parameter settings were enough to produce the desired effect.

A total of three dogs were studied. LV tissue from three normal (NL) dogs and three dogs untreated HF dogs was used for comparison. LV tissue obtained at sacrifice was used to extract total RNA. By use of specific primers in reverse transcriptase-polymerase chain reaction (RT-PCR), B-Type and A-Type natriuretic peptides were identified on agarose-ethidium gel; corresponding fluorescent bands were quantified in densitometric units. The results are shown in the table below:

TABLE 1

|           | NL         | HF-Untreated | HF + CCM    |
|-----------|------------|--------------|-------------|
| B-Type NP | 2590 ± 1339 | 5181 ± 293*  | 2008 ± 796† |
| A-Type NP | 1553 ± 306  | 4976 ± 1025* | 3636 ± 1669† |

*= $P < 0.05$ vs. NL;
†= $P < 0.05$ vs. HF-Untreated

Gene expression of both B-Type and A-Type natriuretic peptides increased in untreated HF dogs compared to NL. CCM Therapy reduced mRNA expression of both B-Type and A-Type natriuretic peptides compared to untreated HF dogs.

Conclusions: The findings indicate that in dogs with HF, four hours of continuous CCM therapy reduces mRNA gene expression of both B-Type and A-Type natriuretic peptides. These findings are consistent with the observed reduction in atrial and ventricular size observed in dogs following CCM therapy.

Example 2

In another example we examined whether four hours of continuous therapy with cardiac contractility modulation (CCM) signals from an OPTIMIZER-II ETC device restores gene expression of bFGF in dogs with HF induced by coronary microembolizations. CCM therapy was previously shown to improve LV ejection fraction (EF) in dogs with HF. CCM leads were implanted on the anterior surface of the LV in an open chest preparation. CCM signal parameters were set to the same values as described above in Example 1. A total of three dogs were studied. LV tissue from three normal (NL) dogs and three dogs untreated HF dogs was used for comparison. LV tissue obtained at sacrifice was used to extract total RNA. By use of specific primers in reverse transcriptase polymerase chain reaction (RT-PCR) and restriction enzyme analysis of the RT-PCR product, bFGF was measured, and bands were quantified in densitometric units. Results are shown in the table below:

TABLE 2

|  | NL | HF-Untreated | HF + CCM |
|---|---|---|---|
| bFGF (densitometric units) | 6099 ± 1486 | 4798 ± 223* | 7600 ± 145† |

\* = p < 0.05 vs. NL;
† = p < 0.05 vs. HF-Untreated mRNA expression for bFGF was significantly reduced in untreated HF dogs compared to NL. CCM therapy was associated with restoration of mRNA expression of bFGF to above normal levels.

Conclusions: In dogs with HF, LV mRNA gene expression of bFGF is decreased compared to NL dogs. Continuous CCM therapy for four hours restored mRNA gene expression for bFGF to above normal level. CCM therapy appears to enhance expression of bFGF and, as such, may be a therapeutic modality that enhances angiogenesis, a condition that is likely to important in the treatment of chronic heart failure and possibly angina pectoris.

Example 3

In yet another experiment, we examined whether four hours of continuous therapy with cardiac contractility modulation (CCM) signals from an OPTIMIZER-II ETC device restores gene expression of aMHC in dogs with HF induced by coronary microembolizations. CCM therapy was previously shown to improve LV ejection fraction (EF) in dogs with HF. CCM leads were implanted on the anterior surface of the LV in an open chest preparation. CCM signal parameters were set to the same values as described above in Example 1. A total of three dogs were studied. LV tissue from three normal (NL) dogs and three dogs untreated HF dogs was used for comparison. LV tissue obtained at sacrifice was used to extract total RNA. Using specific primers in reverse transcriptase polymerase chain reaction (RT-PCR) and restriction enzyme analysis of the RT-PCR product, aMHC was measured and bands were quantified in densitometric units. Results are shown in the table below:

TABLE 3

|  | NL | HF-Untreated | HF + CCM |
|---|---|---|---|
| aMHC (densitometric units) | 3486 ± 351 | 978 ± 63* | 3090 ± 142† |

\* = p < 0.05 vs. NL;
† = p < 0.05 vs. HF-Untreated mRNA expression for aMHC was significantly reduced in untreated HF dogs compared to NL. CCM therapy was associated with restoration of mRNA expression of aMHC to near normal levels.

Conclusions: In dogs with HF, LV mRNA gene expression of aMHC is decreased compared to NL dogs. Continuous CCM therapy for four hours normalized mRNA gene expression for aMHC. Since aMHC is associated with faster velocity of shortening of cardiac muscle compared to the slow-contracting βMHC, this normalization may be responsible, in part, for the observed improvement of LV EF after CCM therapy.

Figure 4:
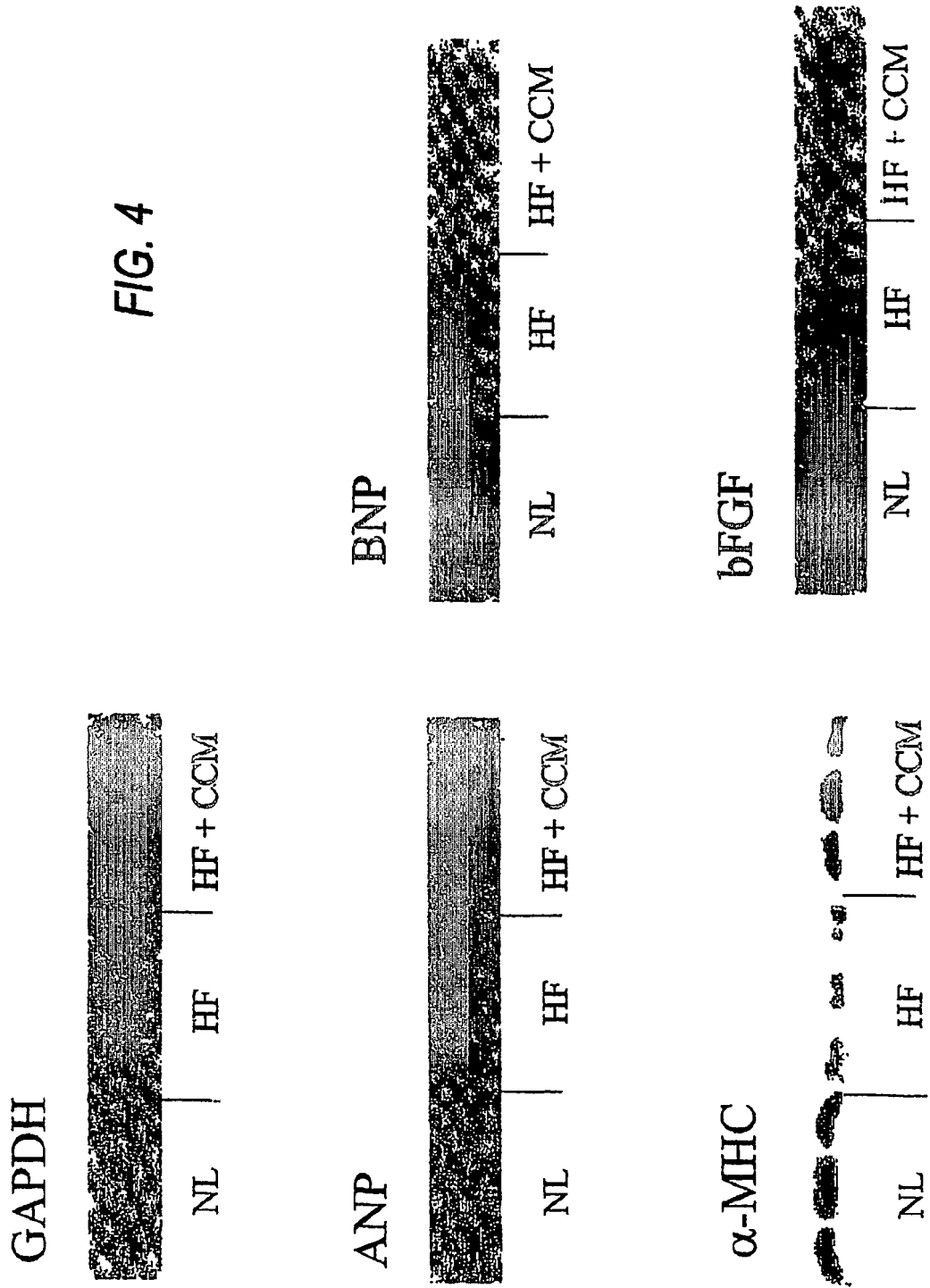
FIG. 4 represents the bands of different genes on agarose-ethidium gel.

The results discussed above are set forth in FIG. 4, which shows the bands of different genes on agarose-ethidium gel. The gel shows the expression levels of GAPDH, a housekeeping gene used to test that the accuracy of the process, and the four different genes previously discussed (ANP, BNP, aMHC, and bFGF)

In each strip there are three groups of bands:
NL—representing the expression in a normal tissue.
HF—representing the expression in heart failure tissue
HF+CCM—representing the expression in HF tissue that was treated with CCM signal for four hours.

Each group contain three different bands coming from three different tissues.

Example 4

Studies were performed in six dogs with coronary microembolization-induced HF. CCM signals were delivered continuously for four hours from epicardial leads placed on the LV anterior wall via a left throracotomy. CCM signal parameters were set to the same values as described above in Example 1. At the end of therapy, tissue samples from the anterior wall were used to extract RNA. Similar tissue samples were taken from 6 normal (NL) and 6 untreated HF dogs. Gene expression for connexin 43 was measured using reverse trascriptase polymerase chain reaction (RT-PCR). The RT-PCR product was confirmed as a connexin 43 by gene sequencing. Bands were quantified in densitometric units and normalized to the housekeeping gene GAPDH.

Results: mRNA expression for GAPDH was similar in all 3 study groups. Connexin 43 mRNA expression decreased markedly in untreated HF dogs compared to NL (0.05±0.002 vs. ±0.62±0.03, P<0.001). CCM therapy partially restored connexin 43 mRNA expression (0.13±0.01, P<0.001).

Conclusions: CCM therapy in dogs with HF increased connexin 43 mRNA expression. These observations may explain, in part, the improvement of LV function and stabilization of electromechanical dysfunction seem following chronic CCM therapy in HF.

While the above described apparatus has focused on hardware, it should be understood that the present invention includes programmable hardware, software for programmable devices, software for programming such hardware and computers including software for programming devices. For example, an external programming station may be provided, which optionally communicates with an implantable device using telemetry. Data collection using telemetry may also be practiced. In addition, computer readable media including such programs are also included. Also included are microcode and other types of programming, as well as hardwired circuitry and ASICs, This is a list of examples and should not be considered as limiting. An exemplary device software includes a decision making module, a timing module, a power module and/or a signal analysis modules.

The description above should not be construed as limiting the scope of the invention to the specific embodiments described, which are provided merely as examples or illustrations. The scope of the invention encompasses interchangeable substitutions that are known to or would be appreciated by those skilled in the art. Many other variations are possible. Thus, the scope of the invention should be determined by the appended claims and their legal equivalents, rather than by only the examples given above.

The invention claimed is:

1. A method for improving heart function comprising electrically modifying the expression in heart tissue of genes that effect cardiovascular system function using an electric field to intentionally both modify the expression and modify a cardiac function, wherein the field is applied to diseased cardiac cells in a heart in which they formed.

2. The method of claim 1, wherein said field is applied by an implantable device adapted to apply a non-excitatory field to a heart in a manner which acutely affects a functioning of said heart, characterized in that the device is adapted to take an effect on gene expression into account in its functioning.

3. The method of claim 2, wherein said device includes a feedback control loop which modifies an application of non-excitatory field in response to an indication of a gene expression effect of a previous application of a non-excitatory field.

4. The method of claim 3, including a watchdog which stops or modifies application of an electrical signal to a heart responsive to an effect of such application on gene expression in the heart.

5. The method of claim 1, wherein said field is applied by an implantable device configured to deliver non-excitatory or non-excitatory and excitatory signals to heart tissue that will modify gene expression of muscle cells in the heart tissue in a way to improve the cardiac function of the cells.

6. The method of claim 1, wherein said field is applied by an implantable device configured to deliver cardiac contractility modulation signals including a non-excitatory contractility modulating component to heart tissue that will modify the expression of BNP and ANP in the heart tissue for treatment of heart failure.

7. The method of claim 1, wherein said field is applied by an implantable device configured to deliver cardiac contractility modulation signals including a non-excitatory contractility modulating component to heart tissue that will normalize the expression of alfa myosin heavy chain aMHC in the heart tissue for treatment of heart failure.

8. The method of claim 1, wherein said field is applied by an implantable device configured to deliver cardiac contractility modulation signals including a non-excitatory contractility modulating component that will modify the expression of basic fibroblast growth factor (bFGF) in the heart tissue for treatment of heart failure.

9. The method of claim 1, wherein the electric field includes an excitatory component.

10. The method of claim 1, wherein the field reduces mRNA gene expression of BNP, ANP, or both BNP and ANP.

11. A method according to claim 10, comprising monitoring said ANP and/or BNP in blood serum.

12. A method according to claim 10, comprising applying said electric field for fewer than 10% of beats in a day.

13. A method according to claim 10, comprising applying said electric field for between 10% and 50% of beats in a day.

14. The method of claim 1, wherein the field modifies mRNA gene expression for bFGF to above normal level.

15. The method of claim 1, wherein the field normalizes nRNA gene expression for aMHC.

16. The method of claim 1, wherein the field reduces mRNA gene expression of BNP, ANP, or both BNP and ANP.

17. The method of claim 1, wherein the field includes a non-excitatory component which causes at least part of said modifying the expression.

18. The method of claim 1, wherein the field includes a non-excitatory component which causes at least part of said modifying the function.

19. A method for treating heart failure comprising electrically modifying the expression in heart tissue of genes that effect cardiovascular system function using an electric field to intentionally both modify the expression and modify a cardiac function, wherein the field is applied to diseased cardiac cells in a heart in which they formed.

20. The method of claim 19, wherein the heart failure is congestive heart failure.

21. The method of claim 19, wherein the electric field includes an excitatory component.

22. The method of claim 19, wherein the field includes a non-excitatory component which causes at least part of said modifying the expression.

23. The method of claim 19, wherein the field includes a non-excitatory component which causes at least part of said modifying the function.

24. A method of treating a patient with a cardiac related disease, comprising:
 determining a desired target gene expression profile in cardiac tissue; and
 applying a non-excitatory signal to the cardiac tissue to modify the gene expression in accordance with the desired target gene expression profile.

25. A method according to claim 24, comprising stopping said applying when said target is reached.

26. A method according to claim 24, wherein said applying comprises applying for at least four hours.

27. A method for improving heart function comprising electrically modifying the expression in heart tissue of genes that effect cardiovascular system function using an electric field that both modifies the expression over a long term and acutely improves cell function of said heart, wherein the non-excitatory signal is applied to diseased cardiac cells in a heart in which they formed.

28. The method of claim 27, wherein the field includes a non-excitatory component which causes at least part of said modifying the expression.

29. The method of claim 27, wherein the field includes a non-excitatory component which causes at least part of said modifying the function.

30. A method of treating a patient with heart failure, comprising:
 determining a desired target gene expression profile in cardiac tissue, said profile associated with improvement in cardiac failure; and
 applying a non-excitatory signal to the cardiac tissue to modify the gene expression in accordance with the desired target gene expression profile, wherein the non-excitatory signal is applied to diseased cardiac cells in a heart in which they formed.

31. The method of claim 30, wherein applying comprises applying said signal at a voltage of between 3 and 15 volts.

32. The method of claim 31, wherein applying comprises applying said signal, at a delay of between 20 and 100 milliseconds from a local activation.

33. The method of claim 32, wherein applying comprises applying said signal, with a duration of between 10 and 50 milliseconds.

34. The method of claim 33, wherein applying comprises applying said signal to the right side of a ventricular septum.

35. The method of claim 34, wherein applying comprises applying said signal for between 1 and 6 hours a day using an implantable stimulator.

36. The method of claim 32, wherein applying comprises applying said signal, with a duration of between 20 and 40 milliseconds.

37. The method of claim 31, wherein applying comprises applying said signal, at a delay of between 20 and 100 milliseconds from a pacing.

38. The method of claim 30, wherein applying comprises applying said signal for between 1 and 6 hours during a period of a day including at least one break period in said applying.

39. A method of treating a patient with a diseased heart, comprising:
(a) determining a desired target gene expression profile in in-vivo cardiac tissue of a diseased heart, said profile associated with improvement in cardiac function; and
(b) applying an electrical signal to diseased cardiac cells formed in the diseased heart to modify the gene expression in accordance with the desired target gene expression profile.

40. A method according to claim 39, wherein said modification in expression lasts after said signal is stopped.

41. A method according to claim 39, wherein a modification in expression lasts at least one week after said signal is stopped.

42. A method according to claim 39, wherein said improvement in cardiac function comprises a reversal in progression of heart failure.

43. A method according to claim 39, wherein said modification in expression comprises a normalization of said profile.

44. A method according to claim 39, wherein said improvement in cardiac function comprises an improvement in contractility.

45. A method according to claim 39, wherein said improvement in cardiac function comprises a reduction in arrhythmia.

46. A method according to claim 39, wherein said applying also has an immediate beneficial effect on cardiac function.

47. A method according to claim 39, wherein said applying does not have an immediate beneficial effect on cardiac function.

48. A method according to claim 39, wherein said signal includes a non-excitatory electrical component which provides at least part of said modifying.

49. A method according to claim 39, comprising closing a loop on said applying using an implantable device.

50. A method according to claim 39, wherein said applying comprises applying after identifying a protocol of applying expected to provide a modification in accordance with said desired gene expression profile.

51. A method according to claim 39, comprising repeating said applying to maintain said modifying of said gene expression profile.

52. A method according to claim 39, comprising repeating said applying to achieve said desired gene expression profile.

* * * * *